United States Patent
Boenitz-Dulat et al.

(10) Patent No.: US 11,306,302 B2
(45) Date of Patent: Apr. 19, 2022

(54) SOLUBLE SORTASE A

(71) Applicant: Hoffmann-La Roche Inc., Little Falls, NJ (US)

(72) Inventors: Mara Boenitz-Dulat, Tutzing (DE); Martin Schatte, Karlsbad (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/933,705

(22) Filed: Mar. 23, 2018

(65) Prior Publication Data

US 2018/0216091 A1    Aug. 2, 2018

Related U.S. Application Data

(63) Continuation of application No. PCT/EP2016/072502, filed on Sep. 22, 2016.

(30) Foreign Application Priority Data

Sep. 25, 2015 (EP) .................................. 15186951

(51) Int. Cl.
*C12N 9/52* (2006.01)
*C12P 21/02* (2006.01)

(52) U.S. Cl.
CPC ............... *C12N 9/52* (2013.01); *C12P 21/02* (2013.01); *C12Y 304/2207* (2013.01); *C07K 2319/30* (2013.01)

(58) Field of Classification Search
None
See application file for complete search history.

(56) References Cited

U.S. PATENT DOCUMENTS

| 8,247,198 | B2 | 8/2012 | Gorke et al. |
| 10,864,277 | B2 | 12/2020 | Grawunder et al. |
| 2009/0117628 | A1 | 5/2009 | Gorke et al. |
| 2014/0030697 | A1 | 1/2014 | Ploegh et al. |
| 2014/0057317 | A1 | 2/2014 | Liu et al. |
| 2016/0193355 | A1 | 7/2016 | Qin et al. |

FOREIGN PATENT DOCUMENTS

| WO | 02/059148 | 1/2002 |
| WO | 2007/140371 A2 | 6/2007 |
| WO | 2010/099536 A2 | 2/2010 |
| WO | 2010/099536 A3 | 2/2010 |
| WO | 2010/087994 A2 | 5/2010 |
| WO | 2012/145522 | 10/2012 |
| WO | 2013/016653 A1 | 1/2013 |
| WO | 2013/003555 A1 | 3/2013 |
| WO | 2013/153203 | 10/2013 |
| WO | 2013/177231 | 11/2013 |
| WO | 2014/001324 A1 | 1/2014 |
| WO | 2014/001325 A1 | 1/2014 |
| WO | 2014/131906 A1 | 4/2014 |
| WO | 2014/177042 | 6/2014 |
| WO | 2014/145441 | 9/2014 |
| WO | 2014/055936 | 10/2014 |
| WO | 2014/183066 A2 | 11/2014 |

OTHER PUBLICATIONS

Caroline Garandeau (The Sortase SrtA of Listeria monocytogenes Is Involved in Processing of Internalin and in Virulence. Infection and Immunity, Mar. 2002, p. 1382-1390) (Year: 2002).*
Hongyuan Mao Sortase-Mediated Protein Ligation: A New Method for Protein Engineering. J. Am. Chem. Soc. 2004, 126,2670-2671. (Year: 2004).*
Database accession No. UNIPROT:A0A0B8RCN4 SubName: Full= Cysteine protease {ECO:0000313:EMBL:GAM94542.1}; SubName: Full=Sortase {ECO:00003131EMBL:AGR15336.1}; SubName: Full= Sortase A {ECO:0000313:EMBL:AKK25356.1} Sep. 16, 2015.
Database accession No. UNIPRO:AOAOE1R5I2, (SubName: Full= Putative cysteine protease ywpE {ECO:00003131EMBL:CCO63533.1}; EC=3.4.22.—{ECO:00003131EMBL:CCO63533.1};) May 27, 2015.
Database accession No. UNIPROT:A9LY59, SubName: Full= Sortase A {ECO:0000313:EMBL:ABX11549.1}; Flags: Fragment; Feb. 5, 2008.
Guimaraes et al., "Site-specific C-terminal and internal loop labeling of proteins using isortase-mediated reactions" Nature Protocols 8:1787-1799 ( 2013).
ISR for PCT/EP2016/072502 (Date of mailing Nov. 8, 2016).
Kyoui et al., "Genetic distance in the whole-genome perspective on Listeria monocytogenes strans F2-382 and NHS-28 that show similar subtyping results" BMC Microbiology 14:309 ( 2014).
Nguyen et al., "Establishment of an experimental system allowing immobilization of proteins on the surface of Bacillus subtilis cells" Journal of Biotechnology 122:473-482 (2006).
Jiang et al., "Research Progress on Sortase and its Application in Biotechnology" Current Biotechnology 1(3):184-188 (2011).
Abbot, A., et al., "Processing of Leather Using Deep Eutectic Solvents" ACS Sustainable Chem Eng 3(6):1241-1247 (Apr. 20, 2015).
Antos et al., "Site-Specific N- and C-Terminal Labeling of a Single Polypeptide Using Sortases of Different Specificity" Journal of the American Chemical Society 131:10800-10801 (2009).
Antos, John M., et al. "Supporting Information" Title: Site-specific N- and C-Terminal labeling of a single polypeptide using sortases of different specificity, Whitehead Institute for Biomedical Research, 9 Cambridge Center, Cambridge, MA 02142, pp. S1-S20 (2009).
Biswas et al., "Sorting of LPXTG Peptides by Archetypal Sprtase A: Role of Invariant Substrate Residues in Modulating the Enzyme Dynamics and Conformational Signature of a Productive Substrate" Biochemistry 53(15):2515-2524 (2014).
Branden et al., Introduction to Protein Structure "Prediction, Engineering, and Design of Protein Structures" New York: Garland Publishing Inc.,:247 (1991).

(Continued)

*Primary Examiner* — Kagnew H Gebreyesus
(74) *Attorney, Agent, or Firm* — Nicole Fortune

(57) ABSTRACT

Herein is reported a polypeptide comprising the amino acid sequence of SEQ ID NO: 38 as sole *Listeria monocytogenes* derived polypeptide and its use in conjugating polypeptides.

7 Claims, 4 Drawing Sheets

Specification includes a Sequence Listing.

(56) References Cited

OTHER PUBLICATIONS

Clancy et al., "Sortase Transpeptidases: Insights into mechanism, substrate specificity and inhibition" Peptide Science 94(4):385-396 (2010).
Clancy, K., et al., "Sortase transpeptidase: Insights into mechanism, substrate specificity, and inhibition" Biopolymers 94(4):385-396 (Jun. 30, 2010).
Dai, Y et al. Natural Deep Eutectic Solvents and Their Application in Natural Product Research and Development, Dissertation "3"Universiteit Leiden, (Sep. 24, 2013).
Durand et al., "Deep eutectic solvents: Synthesis, application, and focus on lipase-catalyzed reactions" Eur. J. Lipid Sci. Technol. 115:379-385 (2013).
Frankel et al., "*Staphylococcus aureus* Sortase Transpeptidase SrtA: Insight into the Kinetic Mechanism and Evidence for a Reverse Protonation Catalytic Mechanism" Biochemistry 44(33):11188-11200 (2005).
Garcia et al., "Deep Eutectic Solvents: Physicochemical Properties and Gas Separation Application" Energy & Fuels 29:2616-2644 (2015).
Gaspar, A., et al., "*Baccillus anthracis* Sortase A (SrtA) Anchors LPXTG Motif-Containing Surface Proteins to the Cell Wall Envelope" J Bacteriol 187(13):4646-4655 (Jul. 1, 2005).
Heck et al., "Continuous Monitoring of nzymatic Reactions on Surfaces by Real-Time Flow Cytometry: Sortase A Catalyzed Protein Immobilization as a Case Study" Bioconjugate Chemistry 25(8):1492-1500 (2014).
Hess et al., "M13 Bacteriohage Display Framework that Allows Sortase-Mediated Modification of Surface-Accessible Phage Proteins" Bioconjugate Chemistry 23:1478-1487 (2012).
Huang et al., "Deep eutectic solvents can be viable enzyme activators and stabilizers" Journal of Chem. Technol Biotechnol 89:1875-1981 (2014).
International Search Report for PCT/EP2015/079692 dated Mar. 16, 2016.
International Search Report of PCT/EP2015/079615 dated Mar. 14, 2016.
ISR and Written Opinion of PCT/EP2016/072512 (dated Nov. 17, 2016).
ISR for PCT/EP2016/072510 (Date of mailing Nov. 15, 2016).
Levary et al., "Protein-Protein Fusion Catalyzed by Sortase A" PLoS One 6(4 Suppl e18342): 1-6 (2011).
Li et al., "A novel reporter system monitoring Sortase A catalyzed protein ligation efficiency" Chinese Journal of Biotechnology 30(2):284-293 (2014).
Li et al., "Irreversible Site-Specific Hydrazinolysis of Proteins by Use of Sortase" Angewandte Chemie International Edition in English 53:2198-2202 (2014).
Lindberg et al., "Deep eutectic solvents (DESs) are viable cosolvents for enzyme-catalyzed epoxide hydrolysis" Journal of Biotechnology 147:169-171 (2010).
Ling, J., et al., "Protein Thioester Synthesis Enabled by Sortase" J Am Chem Soc 134(26):10749-10752 (Jun. 11, 2012).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 (2012).
Marranffini et al., "Anchoring of Surface Proteins to the Cell Wall of *Staphylococcus aureus*" Journal of Biological Chemistry 279(36):37763-37770 (Sep. 3, 2004).
Marraffini et al., "Sortases and the Art of Anchoring Proteins to the Envelopes of Gram-Positive Bacteria" Microbiology and Molecular Biology Reviews 70:192-221 (2006).
Marvin et al., "Recombinant approaches to IgG-like bispecific antibodies" Acta Pharmacologica Sinica 26(6):649-658 (Jun. 2005).
Matsumoto et al., "Site-Specific Tetrameric Streptavidin-Protein Conjugates Using Sortase A" Journal of Biotechnology 152:37-42 (2011).
Matsumoto et al., "Sortase A-Catalyzed Site-Specific Coimmobilization on Microparticles via Streptacidin" Langmuir 28(7):3553-3557 (2012).
Maugeri, Z., et al., "Chymotrypsin-Catalyzed Peptide Synthesis in Deep Eutectic Solvents" Eur J Org Chem 20:4223-4228 (Jun. 4, 2013).
Meissner, P. et al. et al., "Transient gene expression: recombinant protein production with suspension-adapted HEK293-EBNA cells" Biotechnol Bioeng 75:197-203 (2001).
NCBI Database. 002984641.1, (sortase SrtA [*Streptococcus pyogenes*], pp. PN 171203 May 2013.
NCBI Database, 031862293.1 (sortase A [*Staphylococcus aureus*], pp. PN 171203 Sep. 2014.
Oteng-Pabi et al., "Continuous enzyme-coupled assay for micrbial transglutaminase activity" Analytical Biochemistry 441(2):169-173.
Popp et al., "Making and Breaking Peptide Bonds: Protein Engineering Using Sortase" Angew. Chem. Int. Ed. 50:5024-5032 (2011).
ISR for PCT/EP2017/052318 (May 4, 2017).
Popp et al., "Sortase-catalyzed transformations that improve the properties" PNAS 108:3169-3174 (2011).
Race et al., "Crystal Structure of *Streptococcus pyogenes* Sortase A Implications for Sortase Mechanism" Journal of Biological Chemistry 284:6924-6933 (2009).
Sadowski et al., "The sequence-structure relationship and protein function prediction" Current Opinion in Structural Biology 19:357-362 (2009).
Schmohl, L. et al., "Sortase-mediated ligations for the site-specific modification of proteins"Curr Opin Chem Biol 22:122-128 (Oct. 1, 2014).
Seffernick, J. et al., "Melamine Deaminase and Atrazine Chlorohydrolase: 98 Percent Identical but Functionally Different" Journal of Bacteriology 183(8):2405-2410 (2001).
Smith, E., et al., "Deep Eutectic Solvents (DESs) and Their Applications" Chem Rev 114(21):11060-11082 (Oct. 10, 2014).
Strijbis, K. et al., "Protein Ligation in Living Cells Using Sortase" Traffic 13:780-789 (2012).
Sutherland and Durand, Recent Results Cancer Res 95:24-49 (1984).
Ta et al., "Enzymatic Single-Chain Antibody Tagging A Universal Approach to Targeted Molecular Imaging and Cell Homing in Cardiovascular Disease" Circulation Research 109:365-373 (2011).
Tan et al., "Applications of Transpeptidase Sortase A for Protein Modifications" Progress in Chemistry 26(10):1741-1751 (2014).
Tang et al., "Identification of Dehalobacter reductive dehaloenases that catalyse dechlorination of chloroform, 1,1,1-trichloroethane and 1,1-dichloroethane" Philosophical Transactions of The Royal Society B 368:1-10 (2013).
Tang et al., "Recent developments in deep eutectic solvents in chemical sciences" Monatsh Chem. 144:1427-1454 (2013).
Ton-That et al., "Anchoring od Surface Proteins to the Cell Wall of *Staphylococcus aureus*" Journal of Biological Chemistry 277(9):7447-7452 (2002).
Ton-That et al., "Anchoring od Surface proteins to the cell wall of *Staphylococcus aureus*. Sortase catalyzed in vitro transpeptidation reaction using LPXTG peptide and NH(2)-Gly(3) substrates" The Journal of biological chemistry 275(13):9876-81 (2002).
Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).
Tsukiji et al., "Sortase-Mediated Ligation: A Gift from Gram-Positive Bacteria to Protein Engineering" ChemBioChem 10:787-798 (2009).
Walsh, Christopher Antibiotics: actions, origins, resistance Washington, D.C.: ASM Press, (2003).
Witkiowski, A. et al., "Conversion of a â-Ketoacyl Synthase to a Malonyl Decarboxylase by Replacement of the Active-Site Cysteine with Glutamine" Biochemistry 38:11643-11650 (1999).
Written Opinion for PCT/EP2017/052318.
Yamamura et al., "Enhancement of Sortase A-Mediated Protein Ligation by Inducing a beta-Hairpin Structure around the Ligation Site" Chem. Commun. 47:4742-4744 (2011).
Zhang et al., "Deep eutectic solvents: synthesis, properties and applications" Chem Soc Rev 41:7108-7146 (2012).

(56) References Cited

OTHER PUBLICATIONS

Zhao et al., "Choline-based deep eutectic solvents for enzymatic preparation of biodiesel from soybean oil" Journal of Molecular Catalysis B: Enzymatic 85-86:243-247 (2013).
Zhao et al., "Protease activation in glycerol-based deep eutectic solvents" J Mol Catal B Enzym. 72:163-167 (2011).
Bierne et al., "Inactivation of the srtA gene in Listeria monocytogenes inhibits anchoring of surface proteins and affects virulence" Molecular Microbiology 43(4):869-881 (2002).
Bolken et al., "Inactivation of the srtA gene in *streptococcus gordonii* inhibits cell wall anchoring of surface proteins and decreases in vitro and in vivo adhesion" Infection and Immunity 69(1):75-80 (2001).
Chan et al., "Covalent attachment of proteins to solid supports and surfaces via sortase-mediated ligation" PlosOne(11):e1164 (2007).
Dawson et al., "Synthesis of Native Proteins by Chemical Ligation" Annu. Rev. Biochem 69:923-60 (2000).
Dhar et al., "Anchor Structure of cell wall surface proteins in listeria monocytogenes" Biochemistry 39(13):3725-3733 (2000).
Fischetti et al., "Conservation of a hexapeptide sequence in the anchor region of surface proteins from Gram-positive cocci" Molecular Microbiology 4(9):1603-1605 (1990).
Glaser et al., "Comparative genomics of listeria species" Science 294:849-852 (2001).
Ilangovan et al., "Structure of sortase, the transpeptidase that anchors proteins to the cell wall of *Staphylococcus aureus*" Proceedings of the National Academy of Sciences 98(11):6056-6061.
Kruger et al., "Analysis of the substrate specificity of the *staphylococcus aureus* sortase transpeptidase SrtA" Biochemistry 43(6):1541-1551 (2004).
Mao et al., "Sortase-Mediated protein ligation: A new method for protein engineering" Journal of American Chemical Society 126:2670-2671 (2004).
Mazmanian et al., "Sortase-catalysed anchoring of surface proteins to the cell wall of *Staphylococcus aureus*" Molecular Microbiology 40(5):1049-1057 (2001).
Mazmanian et al., "*Staphylococcus aureus* Sortase, an enzyme that anchors surface proteins to the cell wall" Science 285:760-763 (1999).
Pallen et al., "An Embarrassment of sortases—a richness of substrates?" Trends in Microbiology 9(3):97-101 (2001).
Parthasarathy et al., Bioconjugate Chem 18:469-476 (2007).
Samantaray et al., "Peptide-sugar ligation catalyzed by transpeptidase sortase: A facile approach to neoglycoconjugate synthesis" Journal Am. Chem. Soc. 130:2132-2133 (2008).
Yan et al., "Synthesis of Peptides and Proteins without Cysteine Residues by Native Chemical Ligation Combined with Desulfurization" Journal Am. Chem. Soc. 123:526-533 (2001).
Swee et al., "Sortase-mediated modification of alphaDEC206 affords optimization of antigen presentation and immunization against a set of viral epitopes" PNAS 110(4):1428-1433 (2013).
Tanaka et al., "Site-Specific Protein Modification on Living Cells Catalyzed by Sortase" ChemBioChem 9:802-807 (2008).
Witte et al., "Preparation of unnatural N-to-N and C-to-C protein fusions" PNAS 109(30):11993-11998 (2012).

* cited by examiner

SOLUBLE SORTASE A

Herein is reported a novel soluble Sortase A derived from a hitherto unknown *Listeria monocytogenes* Sortase A.

SEQUENCE LISTING

This application contains a Sequence Listing which has been submitted via EFS-Web and is hereby incorporated by reference in its entirety. Said ASCII copy, created on Feb. 27, 2018, is named Sequence_Listing.txt and is 32,264 bytes in size.

BACKGROUND OF THE INVENTION

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthesized peptides to recombinantly expressed proteins.

Applicable Sortases for technical bioconjugation are limited. The most wildly used *Staphylococcus aureus* Sortase A (St.au. SrtA) shows suitable conversion kinetics for technical application but has a limited substrate spectrum, only recognizing LPXTG sortase-motives. The St.au. SrtA, that lacks the N-terminal membrane-anchoring motif, has been used for cell-surface protein labeling, covalent protein immobilization and incorporation of novel functionality into proteins. For orthogonal/dual labeling strategies, sortases with new substrate spectra are needed. The same holds true for standard sortase mediated bioconjugation approaches where a LPXTG motive in the product has e.g. negative effects on its structure and/or function. Therefore sortases with recognition sequences different from LPXTG would be of high value. The *Streptococcus pyogenes* SrtA (St.py. SrtA) recognizes a LPXTA sortase-motives, however the conversion kinetic parameter of the enzyme turn it in to a not suitable sortase on a technical scale.

Sortases that accept sortase-motives different from LPXTG are reported in literature. Thereunder are wild-types e.g. Sortase A from *Streptococcus pyogenes* (St.py. SrtA) and Sortase A from *Clostridium difficile* (Cl.di. SrtA) as well as engineered sortase. Beside the St.py. SrtA none of the reported sortase recognizes a LPXTA motif (see e.g. van Leeuwen, H. C., et al., FEBS Lett. 588 (2014) 4325-4333; Dorr, B. M., et al., Proc. Natl. Acad. Sci. USA 111 (2014) 13343-13348; Bentley, M. L., et al., J. Biol. Chem. 282 (2007) 6571-6581; Race, P. R., et al., J. Biol. Chem. 284 (2009) 6924-33; Antos, J. M., et al., J. Am. Chem. Soc. 131 (2009) 10800-10801).

In WO 2010/087994 methods for ligation and uses thereof are reported. Recombinant approaches to IgG-like bispecific antibodies are reported by Marvin, J. S., et al. (Acta Pharmacol. Sinica 26 (2005) 649-658). In WO 2013/003555 the use of sortases to install click chemistry handles for protein ligation is reported.

Strijbis, K. et al (Traffic 13 (2012) 780-789) report protein ligation in living cells using sortase. It has been stated by them that the $Ca^{2+}$-dependent *S. aureus* sortase A is not functional intracellularly, but that the $Ca^{2+}$-independent *S. pyogenes* sortase A is functional in the cytosol and endoplasmic reticulum (ER) lumen of both *Saccharomyces cerevisiae* and mammalian HEK293T cells.

Levary, D. A., et al., report protein-protein fusion catalyzed by Sortase A (PLOS ONE 6 (2011)). Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). Engineered proteins with high affinity for DOTA chelates are reported in WO 2010/099536.

Different efforts to block the revers reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate.

Sorting of LPXTG peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

Ling and co-workers showed the introduction of a thioester via a sortase (Ling, J. J. J., et al., J. Am. Chem. Soc. 134 (2012) 10749-10752).

Bellucci, J. J., et al. report the use of lysine as nucleophile (Angew. Chem. Int. Ed. Engl. 53 (2014) 1-6).

In Uniprot accession number A0A0E1R5I2_LISMN a putative cysteine protease is reported. A sortase A from *Listeria monocytogenes* comprising 119 residues is reported in Uniprot accession number A9LY59_LISMN.

In WO 2014/183066 a method of conjugating an agent to an animal cell, the method comprising contacting an animal cell with a sortase substrate that comprises a sortase recognition sequence and an agent in the presence of a sortase under conditions suitable for the sortase to conjugate the sortase substrate to an endogenous, non-engineered polypeptide expressed by the animal cell is reported.

A method for producing an antibody Fc-region conjugate, which comprises as first component a recombinant antibody Fc-region and as second component at least one recombinant binding entity that specifically binds to a target, using a sortase A for enzymatic conjugation of the antibody Fc-region to the at least one binding entity is reported in WO 2014/001325.

Site-specific C-terminal internal loop labeling of proteins using sortase-mediated reactions has been reported by Guimaraes, C. P., et. al (Nat. Protoc. 8 (2013) 1787-1799). Nguyen, H. D. and Schumann, W. reported the establishment of an experimental system allowing immobilization of proteins on the surface of *Bacillus subtilis* cells (J. Biotechnol. 122 (2006) 473-482).

SUMMARY OF THE INVENTION

Herein is reported a novel soluble Sortase A derived from a hitherto unknown *Listeria monocytogenes* Sortase A with a high activity against the sortase-motif (sortase recognition sequence) LPXTA (SEQ ID NO: 41, wherein X can be any amino acid residue).

It has been found that a specifically N-terminally truncated soluble variant of a novel *Listeria monocytogenes* Sortase A has increased enzymatic activity compared to other N- or C-terminally truncated variants of the same novel *Listeria monocytogenes* Sortase A.

One aspect as reported herein is a polypeptide comprising the amino acid sequence of SEQ ID NO: 38. In this polypeptide only the amino acid sequence of SEQ ID NO: 38 is/has been obtained from *Listeria monocytogenes*. In one embodiment the amino acid sequence of SEQ ID NO: 38 is the sole *Listeria monocytogenes* derived amino acid sequence in the polypeptide.

In one embodiment the polypeptide comprises additionally a tag at its N- or C-terminus either conjugated directly or via an intervening linker.

In one embodiment the polypeptide is consisting of the amino acid sequence of SEQ ID NO: 38 and the C-terminal tag of SEQ ID NO: 32. In one embodiment the polypeptide is consisting of the amino acid sequence of SEQ ID NO: 38.

In one embodiment the polypeptide is a sortase A.

One aspect as reported herein is a (fusion) polypeptide comprising one domain that has the amino acid sequence of SEQ ID NO: 38 and one or more further domains, wherein the domains are conjugated to each other either directly or via a peptidic linker. In one embodiment the domain that has the amino acid sequence of SEQ ID NO: 38 and (each/any of) the further domains are (obtained from) polypeptides from different organisms and/or are synthetic/artificial polypeptides. In one embodiment the domain that has the amino acid sequence of SEQ ID NO: 38 and the one or more further domains are from different organisms/do not exist in this combination in nature.

One aspect as reported herein is the use of a polypeptide as reported herein for the conjugation of a sortase-motif comprising first polypeptide with a second polypeptide comprising i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues.

One aspect as reported herein is a method for the (enzymatic) production of a (fusion-)polypeptide comprising the following step incubating

- i) a first polypeptide comprising (optionally within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
- ii) a second polypeptide that comprises i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and
- iii) a polypeptide as reported herein, and thereby producing a (fusion-)polypeptide.

In one embodiment the method is for the enzymatic conjugation of two polypeptides.

In one embodiment the second polypeptide has at its N-terminus the amino acid sequence GGG, AAA, CGG, CAA, KGG or KAA.

In one embodiment the first polypeptide comprises at its C-terminus the amino acid sequence LPXTG (SEQ ID NO: 01, wherein X can be any amino acid residue) or LPXTA (SEQ ID NO: 41, wherein X can be any amino acid residue). In one embodiment the first polypeptide comprises at its C-terminus the amino acid sequence LPETG (SEQ ID NO: 04) or LPETA (SEQ ID NO: 42) or LPKTG (SEQ ID NO: 43) or LPKTA (SEQ ID NO: 44).

In one embodiment the first polypeptide and the second polypeptide are independently of each other selected from an antibody variable domain, an antibody heavy chain Fab-fragment, an antibody Fc-region, a tag, and a peptide or polypeptide, a linker and a non-sortase motif moiety, each first polypeptide comprising the amino acid sequence LPXTG (SEQ ID NO: 01, wherein X can be any amino acid residue) or LPXTA (SEQ ID NO: 41, wherein X can be any amino acid residue).

DETAILED DESCRIPTION OF THE INVENTION

The current invention is based at least in part on the finding that N-terminally and N- and C-terminally truncated variants of a novel *Listeria monocytogenes* sortase A unexpectedly differ in their enzymatic activity.

I. Definitions

The term "derived from" denotes that the respective amino acid sequence comprises the same amino acid sequence, or contains amino acid sequence changes, or is a shortened variant or a fused variant of a parent amino acid sequence.

The term "a glycinyl, an alaninyl, or a cysteinyl compound" denotes a compound that comprises a glycine or an alanine or a cysteine amino acid residue with free alpha amino group, e.g. as $NH_2$ or $NH_3^+$, and a carboxy group at position 1 that is in a peptide bond with another moiety, whereby the moiety can be any amino group containing moiety, such as an isolated amino acid residue, a peptide, a polypeptide, a protein, a small molecule, a dye, or a (chemical or peptidic) linker.

The term "comprising" when used herein expressly includes the term "consisting of".

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (e): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, alpha-amino isobutyric acid and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, HA-tag, Nano-tag, SBP-tag, c-myc-tag, S-tag, SNUT-Tag, NusA, T7, thioredoxin, calmodulin-binding-peptide, cellulose-binding-domain, chitin-binding-domain, GST-tag, or MBP-tag (see, e.g., Amau, J., et al., Prot. Expr. Purif. 48 (2006) 1-13).

In one embodiment the tag is selected from SEQ ID NO: 07 (RRRRR), or SEQ ID NO: 08 (RRRRRR), or SEQ ID NO: 09 (HHHHHH), or SEQ ID NO: 10 (KDHLIHNVH-KEFHAHAHNK), or SEQ ID NO: 11 (DYKDDDDK), or SEQ ID NO: 12 (DYKDHDGDYKDHDIDYKDDDDK), or SEQ ID NO: 13 (AWRHPQFGG), or SEQ ID NO: 14 (WSHPQFEK), or SEQ ID NO: 15 (MDVEAWLGAR), or SEQ ID NO: 16 (MDVEAWLGARVPLVET), or SEQ ID NO: 17 (MDEKTTGWRGGHVVEGLAGELEQLRAR-LEHHPQGQREP), or SEQ ID NO: 18 (EQKLISEEDL), or SEQ ID NO: 19 (KETAAAKFERQHMDS), or SEQ ID NO: 20 (KRRWKKNFIAVSAANRFKKISSSGAL), or SEQ ID NO: 21 (cellulose binding domain), or SEQ ID NO: 22 (cellulose binding domain), or SEQ ID NO: 23 (TNPGV-SAWQVNTAYTAGQLVTYNGKTYKCLQPHT-SLAGWEP SNVPALWQLQ), or SEQ ID NO: 24 (GST-tag), or SEQ ID NO: 25 (MBP-tag), or SEQ ID NO: 32 (MRGSHHHHHHGS).

An "effective amount" of an agent, e.g., a pharmaceutical formulation, refers to an amount effective, at dosages and for periods of time necessary, to achieve the desired therapeutic or prophylactic result.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Enzymatic Conjugation Using Sortase A

A covalent conjugate (i.e. a fusion polypeptide) comprising two in vivo not covalently associated entities can be obtained in vitro by using the enzyme sortase, especially a Sortase A.

Transamidases in general catalyze the formation of a peptide bond (amide bond) between an acyl donor and a nucleophilic acyl acceptor. In order to form a peptide bond the acyl acceptor has to contain a NH2-CH2-moiety. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus* and *Streptomyces*.

Sortases have been classified into 4 classes, designated A, B, C, and D, based on sequence alignment and phylogenetic analysis of 61 sortases from gram-positive bacterial genomes (Dramsi, S., et al., Res. Microbiol. 156 (2005) 289-297). These classes correspond to the following subfamilies, into which sortases have also been classified by Comfort and Clubb (Comfort, D. and Clubb, R. T., Infect. Immun. 72 (2004) 2710-2722): Class A (Subfamily 1), Class B (Subfamily 2), Class C (Subfamily 3), Class D (Subfamilies 4 and 5). The aforementioned references disclose numerous sortases and recognition motifs (see also Pallen, M. J., et al., Trends Microbiol. 9 (2001) 97-101). With this information a person skilled in the art can assign a sortase to the correct class based on its sequence and/or other characteristics such as those described in Dramsi (supra).

Sortase A (SrtA) is a membrane bound enzyme has transamidase activity. It has been identified and isolated from gram-positive bacteria. In vivo Sortase A attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide Science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 01) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. It. Ed. Engl. 50 (2011) 5024-5032).

| year/citation | content |
|---|---|
| 1990 Fischetti et al. Mol. Microbiol. 4 (1990) 1603-1605 | LPETG sortase motif |
| 1999 Mazmanian et al. Science 285 (1999) 760-763 | *Staphylococcus aureus* strain OS2<br>conserved Leu-Pro-X-Thr-Gly (LPXTG) motif<br>srtA gene specifies a protein of 206 amino acids with a potential NH2-terminal signal peptide/membrane anchor sequence and a presumed active-site cysteine at position 184<br>srtA homologs are present in *Actinomyces naeslundii*, *Bacillus subtilis*, *Enterococcus faecalis*, *Staphylococcus aureus*, *Streptococcus mutans*, *Streptococcus pneumoniae*, and *Streptococcus pyogenes*<br>AF162687 discloses coding sequence (frame 1 reading)<br>MKKWTNRLMT IAGVVLILVA AYLFAKPHID NYLHDKDKDE KIEQYDKNVK<br>EQASKDKKQQ AKPQIPKDKS KVAGYIEIPD ADIKEPVYPG PATPEQLNRG<br>VSFAEENESL DDQNISIAGH TFIDRPNYQF TNLKAAKKGS MVYFKVGNET<br>RKYKMTSIRD VKPTDVGVLD EQKGKDKQLT LITCDDYNEK TGVWEKRKIF<br>VATEVK |
| 1999 Ton-That et al. Proc. Natl. Acad. Sci. USA 96 (1999) 12424-12429 | *Staphylococcus aureus* strain OS2<br>*Staphylococcus aureus* Sortase A<br>residues 2-25 deleted (N-terminal signal sequence)<br>MW: 22139 Da<br>mutation C184S abolishes catalytic activity<br>sortase homologs from *Streptococcus pyogenes* (Spyo), *Enterococcus faecalis* (Efea), *Actinomyces naeslundii* (Anei), *Streptococcus mutans* (Smut), *Bacillus subtilis* (Bsub), and *Streptococcus pneumoniae* (SpnA, SpnB, and SpnC)<br>water can resolve acyl-enzyme intermediate |
| 2000 Dhar et al. Biochem. 39 (2000) 3725-3733 | *Listeria monocytogenes* has a peptidoglycan cross-bridge (m-Dpm) which is chemically distinct and much shorter than the pentaglycine cross-bridge of staphylococci<br>*Listeria monocytogenes* Sortase A has the same sortase motif as *Staphylococcus aureus* Sortase A: LPXTG (LPTTG) |
| 2000 | purified recombinant *Staphylococcus aureus* Sortase A |

| | -continued |
|---|---|
| Ton-That et al. J. Biol. Chem. 275 (2000) 9876-9881 | hydrolyzes peptides with LPXTG motif<br>triple G-motif<br>in presence of H2N-GGG exclusive transpeptidation<br>in the presence of amino-donors sortase mediated LPXTG motif cleavage rate was increased<br>Sortase is a 206-amino acid polypeptide with an N-terminal signal sequence/stop transfer domain, is anchored in the cytoplasmic membrane of staphylococci<br>residues 1-25 correspond to N-terminal signal sequence<br>reaction conditions:<br>5 mM amino group nucleophile<br>4.71 µM SrtADN<br>150 mM NaCl, 5 mM CaCl2, 50 mM Tris-HCl, pH 7.5)<br>volume of 520 µl<br>reaction conditions:<br>10 µM fluorescent peptide<br>5 mM amino group nucleophile H2NGGG<br>15 µM SrtADN<br>150 mM NaCl, 5 mM CaCl2, 50 mM Tris-HCl, pH 7.5)<br>volume of 520 µl<br>37° C., 16 h |

TABLE III
Kinetic analysis of $SrtA_{\Delta N}$
Kinetic constants $K_m$, $V_{max}$, and $k_{cat}$ were calculated from the curve fit for the Michaelis-Menten equation using the Lineweaver-Burk plot. Reaction conditions are described in the legend to FIG. 4.

| Nucleophile | $K_m$ µM | $V_{max}$ µM/s | $K_{cat}$ 1/s | $K_m/K_{cat}$ 1/µM · s |
|---|---|---|---|---|
| $H_2O$ | 10.88 | $5.08 \times 10^{-5}$ | $1.06 \times 10^{-5}$ | $9.77 \times 10^{-7}$ |
| $NH_2$-$Gly_3$ | 16.48 | $1.08 \times 10^{-4}$ | $2.27 \times 10^{-5}$ | $1.38 \times 10^{-6}$ |

TABLE IV
The effect of different nucleophiles on the rate of LPXTG peptide cleavage by sortase ($SrtA_{\Delta N}$)

| Nucleophile | M $(s^{-1})^a$ |
|---|---|
| $H_2O$ | 1.84 (±0.11) |
| $NH_2OH$ | 1.91 (±0.07) |
| $NH_2$-Gly | 1.95 (±0.05) |
| $NH_2$-$Gly_2$ | 2.03 (±0.13) |
| $NH_2$-$Gly_3$ | 2.91 (±0.03) |

$^a$Slope of the kinetic curves as shown in FIG. 4. The substrate peptide d-QALPETGEE-e was incubated with $SrtA_{\Delta N}$ and various nucleophiles. Substrate cleavage between the threonine and the glycine was measured as an increase in fluorescence. With the exception of water, all nucleophiles were added at a concentration of 5 mM. Averages were calculated from three independent experiments and standard deviations are reported (parentheses).

| | |
|---|---|
| 2001 Bolken et al. Infect. Immun. 69 (2001) 75-80 | sortase A from *Streptococcus gordonii*<br>252 amino acid residues with N-terminal signal sequence<br>cysteine at position 210<br>12-amino-acid extension at the carboxy-terminus of the *S. gordonii* protein compared to *S. aureus* |
| 2001 Glaser et al. Science 294 (2001) 849-852 | *Listeria monocytogenes* genome contains 41 proteins containing an LPXTG<br>Lm genome contains more LPXTG proteins than any other gram-positive bacterium (*Strep. pyogenes*: 13; *St.au. aureus*: 18) |
| 2001 Ilangovan et al. Proc. Natl. Acad. Sci. USA 98 (2001) 6056-6061 | NMR structure of *St.au. aureus* Sortase A<br>unique b-barrel structure including two short helices and several loops<br>the active-site sulfhydryl of cysteine-184 is poised for ionization by histidine-120, presumably enabling the resultant thiolate to attack the LPXTG peptide<br>conservation of H120 and C184<br>calcium binding near the active site stimulates catalysis<br>stimulation by about 2 mM calcium ions<br>magnesium and manganese ions can substitute for calcium ions<br>sortase with residues 1-29 deleted<br>sortase with residues 1-59 deleted<br>average mass of 16,595.12 Da observed<br>reaction conditions: |

-continued

| | |
|---|---|
| | 2 mM H2N-GGG<br>5 μM sortase N-terminal deletion variant<br>150 mM NaCl, 5 mM CaCl2, 50 mM Tris*HCl pH 7.5<br>reaction volume 520 μL<br>*S. aureus* SrtA residues 26-59 display no amino acid conservation;<br>core SrtA residues 60-206 present in all sortase homologs examined |
| 2001 Mazmanian et al. Mol. Microbiol. 40 (2001) 1049-1057 | *St. aureus* sorting motifs: LPETG, LPDTG, LPKTG, LPNTG, PLAAG, LPKAG, LPQTG<br>*Actinomyces naeslundii, Bacillus anthracis, Bacillus subtilis, Clostridium acetabutylicum, Corynebacterium diphtheria, Enterococcus faecalis, Listeria monocytogenes, Streptococcus mutans, Streptococcus pneumoniae, Streptococcus pyogenes* |
| 2001 Pallen et al. TRENDS Microbiol. 9 (2001) 97-101 | LPXTG like motif, followed shortly by a membrane-spanning hydrophobic domain and a charged carboxy-terminal tail |
| | SC7A8.19            VAGHVDNA--------<br>                               EGPAVFYRLGALEKGSAIEIDRRDGGV-<br>                               AVFTVDAVEVYAADAFPDEKVYGAAD---------<br>                               RPELRVITCGGPYSR-----STGYQGNVV |
| | SCM10.23            VVGHVDNQ--------<br>                               QGPAVFYGLGALKKGNKVEVHRQDGKT-<br>                               AVFEIYGIEVFEKNNFPGDRVYGSKG---------<br>                               SPELRVITCGGGFTK-----QNGYDGNVV |
| | SC5C11.07           IAGHVDTK--------<br>                               TSAAVFARLDQLDKGDKFQVRRADGRS-<br>                               ATFVVDGLETFAKDEFPSDRVYGDAD---------<br>                               RPEVRLITCAGDYDH----KVKDYTDNLV |
| | SCE20.15c           MVGHVDTE-------TRPAVFYQLSTLEPGQTIRVA<br>                               RDDDEV-AEFTVDDVQVLTRDGFDAQQAYGPRD<br>                               TG-------RSELRLITCGGTFDQ----TTDSYTANVV |
| | BH3596_bachd        LSGHRDT-------------<br>                               VFRDMGKLEIGDDLTVHMPYGS--<br>                               YTYRIVDTEIVDAN----DTSVIRSTAP--------<br>                               DEVLTLSTCYPFNF----IGSAPERYIIY |
| | yhcs_bacsu          LSGHRDT-------------<br>                               VFRRTGELEKGDQLRLLLSYGE--<br>                               FTYEIVKTKIVDKD----DTSIITLQHE--------<br>                               KEELILTTCYPFSY----VGNAPKRYIIY |
| | BH4010_bachd        LSGHRDT-------------<br>                               VFRELGEVGVGDLLIVETATGT--<br>                               HTYRVRKVRIVDED----DRTVIVPKP--------<br>                               RATLTVSTCYPFDF----IGSAPERYILE |
| | slp2_bacan          LSGHRDT-------------<br>                               VFTDLGQLKEKDTLVLEYDNKT--<br>                               YTYEIQKIWITHAD----DRTVIIKKE--------<br>                               EPILTLTTCYPFDY----IGDAPDRYIIE |
| | BH2127_bachd        IAAHRSR---------<br>                               TYGRQFNRLDEVEVGDVITVTTNNHM--<br>                               YRYTVYSITVVEPT----NIDILQHDG--------<br>                               TAPVLTLITCDPVKDP----THRLIVQAEM |
| | slp_cloab           LAGHRSY---------<br>                               TFGEYFNRLGEIGSGDEIDVETVNGT--<br>                               FKYKVYSTKVVLPS----EVHVLDQT--------<br>                               KDPTMTLVTCTPIRIA----THRLIIKAKR |
| | SCH69.20c           LAGHRN----------<br>                               THGEPFRYINKLEPGDPIVVETQDKY--<br>                               FVYKMASILPVTSPS---<br>                               NVSVLDPVPKQSGFKGPGRYITLTTCTPEFTS----<br>                               KYRMIVWGKM |
| | SCH69.19c           LAAHRD----------<br>                               GHGARFHNIDKIEKGDPIVFETKDTW--<br>                               YVYKTYAVLPETSKY---<br>                               NVEVLGGIPKESGKKKAGHYITLTTCTPVYTS----<br>                               RYRYVVWGEL |
| | fap2_actna          ITGHRGL---------<br>                               AEATMFTNLDKVKTGDSLIVEVFGEV--<br>                               LTYRVTSTKVVEPE----ETEALRVEE-------<br>                               GKDLLTLVTCTPLGIN----THRILLTGER |
| | slp4_cordi          ITAHRGL---------<br>                               AEATMFTNLNKVGVGDRFTIEVMGEV--<br>                               LTYEVRETRVVSPE----DTRFLQTQD-------<br>                               DRDLVTLVTCTPLGIN----THRILVTAER |
| | slp2_strpn          ITAHTGL---------<br>                               PTAKMFTDLTKLKVGDKFYVHNIKEV--<br>                               MAYQVDQVKVIEPT----NFDDLLIVP-------<br>                               GHDYVTLLTCTPYMIN----THRLLVRGHR |

```
slp4_strpn      ITAHRGL---------
                PTAELFSQLDKMKKGDIFYLHVLDQV--
                LAYQVDQIVTVEPN----DFEPVLIQH-------
                GEDYATLLTCTPYMIN----SHRLLVRGKR
slp2_enfae      ISGHRGL---------
                PQAKLFTDLPELKKGDEFYIEVNGKT--
                LAYQVDQIKTVEPT----DTKDLHIES-------
                GQDLVTLLTCTPYMIN----SHRLLVRGHR
slp_streq       ISGHRGL---------
                PSAKLFTNIDKLRINDTFTITSLNRT--
                MTYQVDKIATVLPD----DVSLLRIEE-------
                GKDLVTLVTCTPYGVN----THRLLVRGHR
slp2_strpy      ISAHRGL---------
                PSAEMFTNLNLVKKGDTFYFRVLNKV--
                LAYKVDQILTVEPD----QVTSLSGVM-------
                GKDYATLVTCTPYGVN----TKRLLVRGHR
slp1_cordi      ITGHSGL---------
                ANATLFDNLEDVKEHDPIYITVQGET--
                LKYEVDAINVVLPE----DTKLLAPDP-------
                NKDQITLITCTPYAVN----SHRLLVRAHR
slp2_cordi      ITGHTGL---------
                ANSTMFDHLNKAEKGDTFYVQVSGEK--
                LKYVVDQIKVVLPT----ETEDLRPEQ-------
                GKDYITLITCTPYGIN----THRLMVRGHQ
slp3_cordi      LSAHTGL---------
                QNATLWDNLIQIKKGDPVYVAAAGEK--
                LKYEVRNIEVVTPD----KTSLLRRTS-------
                NKDQVTLITCTPYGIN----THRLIITAER
slp5_cordi      LTAHSGI---------
                QKSTFFDNLEKVKKGDAIYVRNIGET--
                LKYQVRDIEIIRPA----EIDRIQPIP-------
                DRDLITLVTCTPYGIN----THRLLVTAER
BH2015_bachd    IAGHRGYRGNR---------
                HFSRLPDVTIGDEVFLHTKEET--FVYKVTDISIIEPT-
                ---DVDVLDDRD-------GKHEITMITCTRSGK------
                QRVAVRGEL
BH0362_bachd    IAGHRGYRGNR---------
                HFSRLPDVTIGDEVFLHTKEET--FVYKVTDISIIEPT-
                ---DVDILDDRD-------GKHEITMITCTRSGK------
                QRVAVRGVL
slp_strmu       LASHEIVFGMTG-----
                SSQMLFSPLERAKEGMEIYLTDKNKV--
                YTYVISEVKTVTPE----HVEVIDNRP-------
                GQNEVTLVTCTDAGAT----ARTIVHGTYK
slp1_strpy      LASHHIFGITG-----
                SSQMLFSPLERAQNGMSIYLTDKEKI--
                YEYIIKDVFTVAPE----RVDVIDDTA-------
                GLKEVTLVTCTDIEAT----ERIIVKGELK
slp1_strpn      LASHHIFGVDN-----
                ANKMLFSPLDNAKNGMKIYLTDKNKV--
                YTYEIREVKRVTPD----RVDEVDDRD-------
                GVNEITLVTCEDLAAT----ERIIVKGDLK
slp1_enfae      LASHRTEDGVS---------
                LFSPLERTKKDELIYITDLSTV--YTYKITSVEKIEPT-
                ---RVELIDDVP-------GQNMITLITCGDLQAT----
                TRIAVQGTLA
BH3294_bachd    VDHHEGFYYDT-LYNRYDVEVFSAYVTTT--
                DFYYIETEFPS-KDDYKAFLNELKKRSV---
                VQTNVEVGE-------EDQIITLSTCDYRLDRD---
                RGRLVVHGKL
slp3_bacan      FMSHRKLYYDT-LFEGYDLEVFSVYTTTT--
                DFYYIETDFSS-DTEYTSFLEKIQEKSL---
                YKTDTTVTA-------GDQIVTLSTCDYALDPE---
                AGRLVVHAKL
slp_staau       YEKHKIIEFDN-KYGKYQLQVFSAYKTTT--
                KDNYIRTDFEN-DQDYQQFLDETKRKSV---
                INSDVNVTV-------KDKIMTLSTCEDAYSET---
                TKRIVVVAKI
slp3_strpy      FNKHKEFSIETKTKQKLKINIFACIQTDAFDSLLFNP
                IDVDI--SSKNEFLNHIKQKSV---QYREILTTN-------
                ESRFVALSTCEDMTT-----DGRIIVIGQI
slp4_strpy      FNKHNKAIIETKERKKLTVTIFACLKTDAFDQLVF
                NPNAITN--QDQQKQLVDYISKRSK--QFKPVKLKH-
                ------HTKFVAFSTCENFST-----DNRVIVVGTI
slp3_strpn      IAGHRAE---------
                PSHVFFRHLDQLKVGDALYYDNGQEI--
                VEYQMMDTEIILPS----EWEKLESVS-------
                SKNIMTLITCDPIPTFN----KRLLVNFER
```

```
slp1_bacan           LAGHNMS---------
                     KKGVLFSDIASLKKGDKIYLYDNENE--
                     YEYAVTGVSEVTPD----KWEVVEDHG--------
                     KDEITLITCVSVKDN----SKRYVVAGDL
ywpe_bacsu           LAGEIHLK---------
                     QKNLLFGPLENIKTGAQIVITDFKKD--
                     YIYSVTSKDIISEM----DADVVEETN--------
                     KKEITLITCDKAVKT----EGRLVVKGEL
slp3_enfae           LASHNAG---------
                     YEGLLFTSLNKVSVGDLVKLNDREGHS-
                     FIYKVKEQKHVDMT----DTTMLNLTR--------
                     KPTLTLITCDQATKT----TGRIIVIAEL
sortase_staau        IAGHTFID--------
                     RPNYQFTNLKAAKKGSMVYFKVGNET--
                     RKYKMTSIRDVKPT----DVGVLDEQKG------
                     KDKQLTLITCDDYNEK----TGVWEKRKIF
slp_shepu            IAGHRDT-------------
                     HFAILKGMTVGRRLALQTAAGKE-
                     IVYQVVATKVVHES----QTELMAPSD--------
                     DNRLTLITCYPFDALQGVAELRFVVQAVP
SCH22A.15c           VLGHVTVG---------RYDGVFRHLAGRR-
                     GERIEARENGT---TAEFTTAVRTVAKDF---
                     PTDDVYGVA---------PELRLITCGPRDGQE---
                     YRDNVIVAEL
slp_clodi            IYGHNMKN----
                     KTMFNNLNKFKDADFFKKNNKIKITLNGKE--
                     FLYDVFSAYIVESDYDYLKTNFNNESD-------
                     YQNYINDITSKSLYKSP----IKVNSNDKI
MTH1829_metth        ILGHRTT----------
                     YSGPFRKIGALRKGDRVIIEDASSSIRYIYTVTSNGD
                     DIRWDY--RTNPVRFSQS------
                     GDARLMLITCYPPGQK----KAAWITHCKL
```

St.au. aureus: LPKTG
St.au. pyogenes: LPITG
Bac. anthracis: LPKTG
Bac. subtilis: LPDTA
Clos. difficile: SPKTG
Clos. acetabutylicum: LPKTG
S. coelicolor: LAETG, LAATG, LAHTG, LASTG
Arthrobacter. sp.: LASTG
A. naeslundii: LPLTG
A. viscosus: LPLTG, LSRTG
S. pneumoniae: LPETG, VPDTG, IPQTG, YPRTG
C. diphtheria: LPMTG, LALTG, LPKTG, LGNTG, LPLTG, LAFTG
S. putrefasciens: LPQTS

| | |
|---|---|
| 2002 Garandeau et al. Infect. Immun. 70 (2002) 1382-1390 | in silico identification of sortase from *L. monocytogenes* 222 amino acid residues TLXTC consensus motif for sortase active site MLKKTIAAAA LAAGLLLIFS PFIKNGIVKY MSGHETIEQY KASDIKKNNE KDATFDFESV QLPSMTSVIK GAANYDKDAV VGSIAVPSVD VNLLVFKGTN TANLLAGATT MRSDQVMGKG NYPLAGHHMR DESMLFGPIM KVKKGDKIYL TDLENLYEYT VTETKTIDET EVSVIDNTKD ARITLITCDK PTETTKRFVA VGELEKTEKL TKELENKYFP SK |
| 2002 Bierne et al. Mol. Microbiol. 43 (2002) 869-881 | *Listeria monocytogenes* BLAST analysis: one sequence that is 28% identical to *S. aureus* SrtA and encodes a protein of 222 amino acids with an expected molecular weight of 24.7 kDa contains a putative signal peptide/transmembrane region, the expected TLXTC sequence and two stretches of 13 and 31 amino acids that are not present in SrtA |
| 2004 Mao et al. J. Am. Chem. Soc. 126 (2004) 2670-2671 | peptide with single aminoglycoside as nucleophile attack 50 times faster than water yield not affected by number of glycine residues 30% yield after 30 min, 50% after 6 h, 90% after 24 h conjugates D-amino acid containing peptide; rate half that for L-amino acid peptides conjugation of small molecules coupled to triglycine (folate) branched peptide as efficiently coupled as linear peptide |
| 2004 Kruger et al. Biochem. 43 (2004) 1541-1551 | SrtA in *Staphylococcus aureus*, *Streptococcus gordonii*, *Listeria monocytogenes*, *Streptomyces coelicolor*, *Streptococcus pyogenes*, *Streptococcus suis* *S. aureus* two sortase isoforms: SrtA, SrtB (MPQTN motif) LPXTG motif highly conserved among all gram-positive bacteria NPQTN motif appears to be conserved only among at least three bacteria containing the heme iron acquisition isd gene locus (*Bacillus anthracis*, *Bacillus halodurans*, and *S. aureus*) *Staphylococcus aureus* Sortase A residues 2-24 deleted transpeptidase reaction conditions: |

| | |
|---|---|
| | 100 µL reaction volume |
| | 150 mM NaCl, 300 mM Tris, 5 mM CaCl2 (pH 7.5), |
| | pentaglycine (2 mM), SrtAΔN24 (840 nM), and 0 to 10 mM Abz- |
| | LPETG-Dap(Dnp)-NH2 |
| | 37° C., 30 min |
| | transpeptidase reaction conditions: |
| | 100 µL reaction volume |
| | 150 mM NaCl, 300 mM Tris, 5 mM CaCl2 (pH 7.5) |
| | SrtAΔN24 (15 µM), Gly5 (2 mM), peptide (300 µM) |
| | 37° C. for 30 min |
| | quenched by 1N HCl (50 µL) |
| | transpeptidase reaction conditions: |
| | 100 µL reaction volume |
| | 150 mM NaCl, 300 mM Tris, 5 mM CaCl2 (pH 7.5) |
| | SrtAΔN24 (60 µM), Gly5 (2 mM), peptide (300 µM) |
| | 37° C. for 360 min |
| | no reaction with inverted sortase motif or SrtB motif |
| | initial velocity motif: LPXTG (X = any except P, C; X = M fastest) |
| | end point motif: L/M-P-X-A/L/S/T/V-G (X = any except P, C; L |
| | better than M; T and A comparable, then S and V and L comparable) |
| | Table 3 sorting signals: LM: IPKTG, IPALG, LAASS, LPATG, |
| | LPKAG, LPISS, IPALG, LPKTS |
| 2007 Parthasarathy et al. Bioconjug. Chem. 18 (2007) 469-476 | conjugation to surface of non-protein species (polystyrene beads, PEG) alkylamine as nucleophile making of cyclic peptides use of 159 amino acid sortase transpeptidase reaction conditions: 50 mM Tris, 150 mM NaCl, pH 8, 0.1% Tween-20, 6 mM CaCl2, 3 mM beta-mercaptoethanol 37° C., 3 h 15 µM eGFP, 10 µM sortase add 10 mM EDTA to stop the reaction transpeptidase reaction conditions: 50 mM Tris, 150 mM NaCl, pH 8 37° C., 3 h 12 µM eGFP-LPETG, 40 µM sortase, 36 µM GGG-eGFP with beads higher concentration of sortase has to be used for comparable yield use of a cleavable upstream tag to protect nucleophile (GGG) enzyme displays a strong preference for glycine in the first position; alanine and valine can apparently substitute for glycine in the second position, although the reaction is not as efficient |
| 2007 Chan et al. PlosOne 11 (2007) e1164 | conjugation to solid supports tetraglycine beads react faster than diglycine beads which react faster than monoglycine beads reaction conditions: 85 µM eGFP-LPETGG-His6 40 nM His6-sortase 50 mM Tris-HCl, 150 mM NaCl, 5 mM CaCl2, pH 7.5 sortase amplified for *S. aureus* genome N-terminal membrane targeting sequence removed 30 kDa on SDS gel |
| 2008 Samantaray et al. J. Am. Chem. Soc. 130 (2008) 2132-2133 | peptide-sugar conjugation 6-aminohexoses peptide antibiotic ligation (aminoglycosides) conjugates between antibiotics and peptides with yields of 35 to 70% for kanamycin class, about 18-30% for ribostamycin class YALPET-sugar adduct YALPMTGK-sugar adduct LPNTG motif with *S. aureus* sortase and peptide |

For the enzymatic conjugation a soluble truncated sortase A lacking the membrane-spanning region (SrtA; amino acid residues 60-206 of *Staphylococcus aureus* SrtA) can be used (SEQ ID NO: 05; see also Ton-That, H., et al., Proc. Natl. Acad. Sci.

USA 96 (1999) 12424-12429; Ilangovan, H., et al., Proc. Natl. Acad. Sci. USA 98 (2001) 6056-6061).

The sortase A-mediated reaction results in the ligation of species containing a sortase motif (sequence) with those bearing one or more N-terminal glycine residues. The sortase motif can be the amino acid sequence LPXTG, but can also different therefrom (see below). However, a drawback of using such sequences as acyl donors is that the transfer of the LPXT unit to a nucleophilic acyl acceptor liberates a stoichiometric amount of a corresponding fragment containing at least one N-terminal glycine residue. The liberated glycine-containing fragment competes with the intended acyl acceptor for the enzymatic intermediate and works against the progress of the enzymatic ligation reaction. Additionally the hydrolytic cleavage of the enzymatic intermediate as well as the LPXTG containing substrate, although a relatively slow process, compete with the reaction. In the beginning of the use of the sortase-mediated reaction useful levels of ligation could only be obtained using concentrations of at least 5 mM of the acyl donor comprising the sortase-motif.

The general sortase-motif has the amino acid sequence LPXT, wherein X can be any amino acid residue, i.e. a naturally occurring amino acid residue or a non-naturally occurring amino acid residue. In some embodiments, X is selected from the group of amino acid residues comprising or consisting of (in one letter code) D, E, A, N, Q, K, and R. In some embodiments, the sortase-motif is selected from the group comprising or consisting of the amino acid sequences LPXT, LPXA, SPXT, LAXT, LSXT, NPXT, VPXT, IPXT, LGXT, and YPXR. In some embodiments, the sortase motif is selected from the group of amino acid sequences consisting of LPST, LPKT, LPIT, LPDT, SPKT, LAET, LAAT, LAET, LAST, LAET, LPLT, LSRT, LPET, VPDT, IPQT, YPRR, LPMT, LPLT, LAFT, and LPQT. In certain embodiments in which sortase A is used, the sortase-motif comprises the amino acid sequence X1PX2X3, wherein i) X1 is selected from the group consisting of the amino acid residues leucine, isoleucine, valine and methionine, ii) X2 is any amino acid, and iii) X3 is selected from the group consisting of threonine, serine and alanine. In specific embodiments, as noted above X1, is leucine and X3 is threonine. In certain embodiments X2 is selected from the group consisting of aspartate, glutamate, alanine, glutamine, lysine and methionine.

In some embodiments the sortase-motif is selected from the group of amino acid sequences comprising or consisting of LPKTG, LPITG, LPDTA, SPKTG, LAETG, LAATG, LAHTG, LASTG, LAETG, LPLTG, LSRTG, LPETG, VPDTG, IPQTG, YPRRG, LPMTG, LPLTG, LAFTG, and LPQTS. In some embodiments of the invention the sortase is a sortase A (SrtA). SrtA recognizes a sortase-motif with the amino acid sequence LPXTG. Common sortase-motif amino acid sequences are, e.g., LPKTG, LPATG, LPETG and LPNTG. In some embodiments LPETG is used. However, sortase-motifs not in line with this consensus sortase-motif amino acid sequence may also be recognized. For example, in some embodiments the sortase-motif comprises the amino acid residue A rather than the amino acid residue T at position 4, e.g. LPXAG or LPNAG. In some embodiments the sortase-motif comprises the amino acid residue A rather than the amino acid residue G at position 5, e.g. LPXTA or LPNTA. In some embodiments the sortase-motif comprises the amino acid residue G rather than the amino acid residue P at position 2, e.g. LGXTG or LGATG. In some embodiments the sortase-motif comprises the amino acid residue I rather than the amino acid residue L at position 1, e.g., IPXTG or IPNTG or IPETG.

In some embodiments, where the sortase-motif is LPXTG or LPXT, X is selected from the group consisting of D, E, A, N, Q, K, and R. In some embodiments X is selected from the group of amino acid residues consisting of K, E, N, Q, and A in an LPXTG or LPXT motif where the sortase is a sortase A. In one embodiment the sortase-motif is LPET or LPETG or LPETA.

In certain embodiments where sortase A from *Staphylococcus aureus* (St.au. SrtA) is used the sortase-motif has the amino acid sequence LPX1TX2, wherein i) X1 is selected from the group of amino acid residues consisting of D, E, A, N, Q, K, and R, and ii) X2 is selected from the group of amino acid residues consisting of alanine and glycine. In certain embodiments the sortase-motif of St.au. SrtA is LPX1TA. In other embodiments the sortase-motif of St.au. SrtA is LPX1TG. X1 has the meaning as outlined before.

*Streptococcus pyogenes* sortase A (St.py. SrtA) will accept di-alanine based nucleophiles. This sortase will efficiently cleave the sortase-motif amino acid sequence LPXTA between the threonine and the alanine residue and install modified alanine-based nucleophiles. St.py. SrtA will also recognize and cleave LPXTG motifs, albeit with reduced efficiency.

*Staphylococcus aureus* sortase A (St.au. SrtA) will not significantly cleave LPXTA motifs or accept alanine based nucleophiles.

In one embodiment, a polypeptide is contacted with Strep. SrtA and an alanine-containing nucleophile. The polypeptide comprises a sortase-motif amino acid sequence that can be recognized by Strep. SrtA at or near its C-terminus and the nucleophile comprises one or more amino acids capable of serving as nucleophile for a St.au. SrtA-mediated reaction at or near its N-terminus (e.g., (G)n, where n is between 1 and 10, e.g., between 1 and 5). This leads to the formation of an LPXTA sequence at the reactive site, a motif refractory to cleavage by St.au. SrtA. This allows for example St.au. SrtA to act on the N-terminus without affecting the C-terminal modification installed with Strep. SrtA.

Sortase fragments having sortase transamidation activity can be used in the methods as reported herein. Sortase fragments can be identified by producing fragments of sortase, for example, by recombinant techniques or proteolytic digestion of full length sortase, and determining the rate of peptide bond formation, i.e. ligation. The fragment can comprise about 80% of amino acid sequence of full-length sortase, about 70%, about 60%, about 50%, about 40% or about 30% of the amino acid sequence of full-length sortase such as that of *S. aureus* Sortase A (GenBank Accession number AAD48437). In some embodiments the fragment lacks an N-terminal portion of the full-length sortase amino acid sequence that is not essential to the catalytic activity of sortase, for example the fragment lacks the N-terminal portion extending to the end of the membrane anchor sequence. In some embodiments the fragment comprises the C-terminus of a full-length sortase amino acid sequence. In some embodiments, the fragment comprises the catalytic core region of a sortase. In one embodiment the core region is from about position 60 to about position 206 of SrtA, e.g., *S. aureus* SrtA, or about from position 82 to about position 249 of Strep. SrtA.

Sortases from other organisms also can be utilized in the processes as reported herein. Such sortases often are encoded by nucleotide sequences substantially identical or similar to the nucleotide sequences that encode SrtA. A similar or substantially identical nucleotide sequence may include modifications to the native sequence, such as substitutions, deletions, or insertions of one or more nucleotides. Included are nucleotide sequences that are at least 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide positions shared between two nucleic acids.

SrtA nucleotide sequences may be used as "query sequences" to perform a search against public databases to identify related sequences. Such searches can be performed using the NBLAST and XBLAST programs (version 2.0) of Altschul, et al. (J. Mol. Biol. 215 (1990) 403-410). BLAST nucleotide searches can be performed with the NBLAST program, score=100, word-length=12 to obtain homologous nucleotide sequences. To obtain gapped alignments for comparison purposes, gapped BLAST can be utilized as described in Altschul, et al. (Nuc. Acids Res. 25 (1997) 3389-3402). When utilizing BLAST and Gapped BLAST programs, default parameters of the respective programs (e.g., XBLAST and NBLAST) can be used (see e.g. www.ncbi.nlm.nih.gov).

A variant amino acid sequence departs from a native amino acid sequence. Amino acid substitutions may be made on the basis of similarity in polarity, charge, solubility, hydrophobicity, hydrophilicity, helix-forming properties and/or amphipathic properties and the resulting variants are screened for enzymatic activity with a suitable assay, such as that reported in European patent application EP14198535. For example, negatively charged amino acids include aspartic acid and glutamic acid; positively charged amino acids include lysine and arginine; and amino acids with uncharged polar or non-polar head groups having similar hydrophilicity values include leucine, isoleucine, valine, glycine, alanine, asparagine, glutamine, serine, threonine, phenylalanine, and tyrosine. In certain embodiments, conservative substitutions may be made, according to the following Table. Amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

| aliphatic amino acid residues | non-polar | G, A, P |
| --- | --- | --- |
| | | I, L, V |
| | polar, non-charged | C, S, T, M |
| | | N, Q |
| | polar, charged | D, E |
| | | K, R |
| aromatic | | H, F, W, Y |

In certain embodiments homologous substitution may occur, which is a substitution or replacement of like amino acids, such as basic for basic, acidic for acidic, polar for polar amino acids, and hydrophobic for hydrophobic, for example.

Non-homologous substitutions can be introduced to a native sequence, such as from one class of residue to another (e. g. a non-hydrophobic to a hydrophobic amino acid), or substituting a naturally occurring amino acid with an unnatural amino acids or non-classical amino acid replacements.

In the methods as reported herein the sortase, the sortase-motif comprising polypeptide (i.e. the acyl donor), and the nucleophile (i.e. the acyl acceptor) are incubated together under conditions suitable to effect the formation of a peptide bond between the N-terminal part of the sortase-motif comprising polypeptide and the nucleophile. As used herein, the term "incubating" or grammatical equivalents thereof denotes that the components of the process are brought in close proximity to one another to allow contact between the molecules. Incubating can be done by adding them to one reaction vessel, for example. The components in the system may be mixed in a variety of manners, such as by oscillating a vessel, subjecting a vessel to a vortex generating apparatus, or repeated mixing with a pipette or pipettes, for example. The components may be added in any order to the system.

The sortase reaction may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364 (1993) 555-556), and microfluidic devices (see, e.g., U.S. Pat. Nos. 6,440,722; 6,429,025; 6,379,974; and 6,316,781).

The reaction mixture is generally cell free and further does not include bacterial cell wall components or intact bacterial cell walls. In some embodiments, the sortase-motif comprising polypeptide and/or the nucleophile are expressed by one or more recombinant nucleotide sequences in a cell, which nucleotide sequences are integrated into the cell genome or non-integrated (e.g., in a plasmid).

The reaction mixture is maintained at any convenient temperature at which the sortase reaction can be performed. In some embodiments, the sortase reaction is performed at a temperature between and including about 15° C. and about 50° C. In some embodiments, the sortase reaction is performed at a temperature between and including about 23° C. and about 37° C. In certain embodiments, the temperature is room temperature (i.e. about 20° C. to 25° C.). The temperature can be optimized by repetitively performing the same sortase reaction at different temperatures and determining ligation rates.

Any convenient volume and component ratio can be used. In certain embodiments, a (molar) ratio of 1:1000 or greater of sortase enzyme to sortase-motif comprising polypeptide is utilized, or a (molar) ratio of 1:1000 or greater of sortase enzyme to nucleophile is utilized. In specific embodiments, ratios of sortase enzyme to sortase-motif comprising polypeptide or enzyme to nucleophile is about 1:1, including 1:2 or greater, 1:3 or greater, 1:4 or greater, 1:5 or greater, 1:6 or greater, 1:7 or greater, 1:8 or greater, and 1:9 or greater.

In some embodiments, the sortase-motif comprising polypeptide is present at a concentration ranging from about 10 µM to about 10 mM. In some embodiments, the sortase-motif comprising polypeptide is present at a concentration ranging from about 100 µM to about 1 mM. In some embodiments, the sortase-motif comprising polypeptide is present at a concentration ranging from about 100 µM to about 50 mM. In some embodiments, the sortase-motif comprising polypeptide is present at a concentration ranging from about 200 µM to about 10 mM. In some embodiments, the sortase-motif comprising polypeptide is present at a concentration ranging from about 200 µM to about 800 µM. In some embodiments, the sortase-motif comprising polypeptide is present at a concentration ranging from about 400 µM to about 600 µM.

In certain embodiments the nucleophile is present in excess with respect to the sortase-motif comprising polypeptide. In certain embodiments, the nucleophile is present in 10-fold excess with respect to the sortase-motif polypeptide. In certain embodiments, the nucleophile is present in 25-fold excess with respect to the sortase-motif polypeptide. In certain embodiments, the nucleophile is present in 50-fold excess with respect to the sortase-motif polypeptide. In certain embodiments, the nucleophile is present in 100-fold excess with respect to the sortase-motif polypeptide. In certain embodiments, the nucleophile is present in 250-fold excess with respect to the sortase-motif polypeptide.

In certain embodiments, the nucleophile is present at a concentration ranging from about 1 µM to about 50 mM. In certain embodiments, the nucleophile is present at a concentration ranging from about 15 µM to about 1500 µM. In certain embodiments, the nucleophile is present at a concentration ranging from about 25 µM to about 1000 µM. In certain embodiments, the nucleophile is present at a concentration ranging from about 40 µM to about 250 µM.

In certain embodiments, the sortase is present at a concentration ranging from about 1 µM to about 500 µM. In certain embodiments, the sortase is present at a concentration ranging from about 15 µM to about 150 µM. In certain embodiments, the sortase is present at a concentration ranging from about 25 µM to about 100 µM. In certain embodiments, the sortase is present at a concentration ranging from about 40 µM to about 60 µM.

In certain embodiments, the method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents sometimes are 20% or less, 15% or less, 10% or less or 5% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the reaction mixture includes only an alcohol or an organic solvent, with only limited amounts of water if it is present.

In some embodiments, the reaction mixture comprises a buffer. A person skilled in the art will be familiar with a variety of buffers that could be used in accordance with the methods as reported herein. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents.

In some embodiments, the method is performed at a pH value in the range of from 6 to 8.5. In some embodiments, the method is performed at a pH value in the range of from 6 to 8. In some embodiments, the method is performed at a pH value in the range of from 6 to 7.5. In some embodiments, the method is performed at a pH value in the range of from 6.5 to 8.5. In some embodiments, the method is performed at a pH value in the range of from 7 to 8.5. In some embodiments, the method is performed at a pH value in the range of from 7.5 to 8.5. In some embodiments, the method is performed at a pH value in the range of from 7.0 to 8.5. In some embodiments, the method is performed at a pH value in the range of from 7.3 to 7.8.

One or more components of the reaction mixture or the product may be immobilized to a solid support. The attachment between the reaction mixture component and the solid support may be covalent or non-covalent (see, e.g., U.S. Pat. No. 6,022,688 for non-covalent attachments). The solid support may be one or more surfaces of the system, such as one or more surfaces in each well of a microtiter plate, a surface of a glass slide or silicon wafer, BIAcore chip, a surface of a particle, e.g., a bead (see e.g., Lam, Nature 354 (1991) 82-84) that is optionally linked to another solid support, or a channel in a microfluidic device, for example. Types of solid supports, linker molecules for covalent and non-covalent attachments to solid supports, and methods for immobilizing molecules to solid supports are known (see, e.g., U.S. Pat. Nos. 6,261,776; 5,900,481; 6,133,436; 6,022, 688; WO 2001/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Any polypeptide, eventually after introduction of a sortase-motif or an oligoglycine or -alanine, may be used as sortase-motif comprising polypeptide or nucleophile in the methods as reported herein.

Summarizing the above, the first substrate, also denoted as donor, comprises the sortase recognition motif. It is cleaved by the sortase after the threonine residue in the recognition motif. Thereby a C-terminal activated carboxyl group (acyl intermediate) is generated. The second substrate, also denoted as acceptor or nucleophile, provides a (free N-terminal) amino group. Between the free amino group and the activated carboxyl group a peptide bond is formed in the sortase catalyzed transpeptidation reaction.

Thus, for the enzymatic sortase mediated transpeptidation reaction it is only required that a donor comprising a sortase recognition motif and an acceptor comprising an N-terminal free glycine, alanine, cysteine or an equivalent functional group is incubated with a polypeptide having sortase A catalytic activity. The remainder of the donor as well as of the acceptor does not interfere with the reaction.

Thus, a sortase mediated transpeptidation reaction can be performed with virtually any protein or small molecule independently of each other as donor or acceptor as long as these comprise a pair of sortase recognition sequence and nucleophile.

This is confirmed by the art.

For example, Marraffini et al. (Microbiol. Mol. Biol. Rev. 70 (2006) 192-221) reported that sortase A can be used to incorporate chemicals containing glycine residues with a free amino group to the LPXTG motif of recombinant proteins, i.e. without limitation of the protein. Presented examples are the conjugation of triglycyl-lysine-folate with (GFP or Cre or p27)-LPETG-His6 with high efficiency, the incorporation of the branched peptide AT-P-022 into polypeptides, and the self-cleavage of chimeras of His6-sortase-LPETG-target protein (the fusion cleaves itself once the enzyme has been activated by the addition of calcium and triglycine).

Further, Antos et al. (J. Am. Chem. Soc. 131 (2009) 10800-10801) reported that the transpeptidation reaction catalyzed by sortase A allows site-specific derivatization of proteins with virtually any type of functional material. Target proteins are engineered to contain the recognition site (LPXTG) near their C terminus, thus allowing a transacylation reaction in which the residues C-terminal to threonine are exchanged for a synthetic oligoglycine peptide. It is reported that the terminal G residue of the sortase recognition motif can be replaced by a methyl ester without imparting the reaction. In this document nucleophiles comprising either a fluorescent label or a protein were used for the conjugation to cholera toxin B subunit.

Further, Popp et al. (Proc. Natl. Acad. Sci. USA 108 (2011) 3169-3174) reported the use of Sortase for polypeptide cyclization and PEGylation. The method is general and applicable to a wide variety of proteins. The sortase transpeptidase reaction allows facile site-specific PEGylation of multiple distinct proteins, as exemplified using interferon a2, GCSF, and erythropoietin. In all cases tested, the site-specific C-terminal PEGylation proceeded efficiently.

In EP 2 990 423 a self-cleaving sortase construct is reported. In this construct the sortase recognition sequence LPETG and the catalytic sortase domain have been combined in the same molecule. As protein comprising the sortase recognition sequence any protein, such as e.g. a protein selected from the group comprising polymer proteins, glycoproteins, cytokines, growth factor, blood preparations, vaccines, hormones, enzymes, antibodies and parts or fragments thereof (isolated light or heavy chains).

III. The New Sortase as Reported Herein

It has been found that a specifically N-terminally truncated soluble variant of a novel *Listeria monocytogenes* Sortase A has increased enzymatic activity compared to other N- or C-terminally truncated variants of the same novel *Listeria monocytogenes* Sortase A.

Full length *Streptococcus pyogenes* Sortase A (Uniprot Q1J6K9; catalytic core underlined; conserved histidine underlined) has the following amino acid sequence:

```
                                       (SEQ ID NO: 33)
MVKKQKRRKI KSMSWARKLL IAVLLILGLA LLFNKPIRNT

LIARNSNKYQ VTKVSKKQIK KNKEAKSTFD FQAVEPVSTE

SVLQAQMAAQ QLPVIGGIAI PELGINLPIF KGLGNTELIY

GAGTMKEEQV MGGENNYSLA SHHIFGITGS SQMLFSPLER

AQNGMSIYLT DKEKIYEYII KDVFTVAPER VDVIDDTAGL

KEVTLVTCTD IEATERIIVK GELKTEYDFD KAPADVLKAF

NHSYNQVST.
```

The amino acid sequence of the mature soluble sortase A derived from *Streptococcus pyogenes* is

```
                                       (SEQ ID NO: 06)
VLQAQMAAQQ LPVIGGIAIP ELGINLPIFK GLGNTELIYG

AGTMKEEQVM GGENNYSLAS HHIFGITGSS QMLFSPLERA

QNGMSIYLTD KEKIYEYIIK DVFTVAPERV DVIDDTAGLK

EVTLVTCTDI EATERIIVKG ELKTEYDFDK APADVLKAFN

HSYNQVST.
```

Full length *Staphylococcus aureus* Sortase A (see Mazmanian et al.; catalytic core underlined; conserved histidine underlined) has the following amino acid sequence:

```
                                       (SEQ ID NO: 26)
MKKWTNRLMT IAGVVLILVA AYLFAKPHID NYLHDKDKDE

KIEQYDKNVK EQASKDKKQQ AKPQIPKDKS KVAGYIEIPD

ADIKEPVYPG PATPEQLNRG VSFAEENESL DDQNISIAGH

TFIDRPNYQF TNLKAAKKGS MVYFKVGNET RKYKMTSIRD

VKPTDVGVLD EQKGKDKQLT LITCDDYNEK TGVWEKRKIF

VATEVK.
```

All *Staphylococcus aureus* Sortases A reported in the art are truncated at the N-terminus in order to remove the transmembrane domain. Ilangovan et al. (Proc. Natl. Acad. Sci. USA 98 (2001) 6056-6061) report that N(2-29)-terminally truncated Sortase A from *Staphylococcus aureus* has the same catalytic activity and shows the same cation dependent activity as N(2-59)-terminally truncated *Staphylococcus aureus* Sortase A (see FIG. 1 of Ilangovan).

*Staphylococcus aureus* Sortase A without the N-terminal 28 amino acid residues (N(2-29) transmembrane domain) has the following amino acid sequence:

```
                                       (SEQ ID NO: 34)
MDNYLHDKDK DEKIEQYDKN VKEQASKDKK QQAKPQIPKD

KSKVAGYIEI PDADIKEPVY PGPATPEQLN RGVSFAEENE

SLDDQNISIA GHTFIDRPNY QFTNLKAAKK GSMVYFKVGN

ETRKYKMTSI RDVKPTDVGV LDEQKGKDKQ LTLITCDDYN

EKTGVWEKRK IFVATEVK.
```

*Staphylococcus aureus* Sortase A without the N-terminal 59 amino acid residues (transmembrane domain) has the following amino acid sequence:

```
                                       (SEQ ID NO: 05)
QAKPQIPKDK SKVAGYIEIP DADIKEPVYP GPATPEQLNR

GVSFAEENES LDDQNISIAG HTFIDRPNYQ FTNLKAAKKG

SMVYFKVGNE TRKYKMTSIR DVKPTDVGVL DEQKGKDKQL

TLITCDDYNE KTGVWEKRKI FVATEVK
```

Alignment of *Staphylococcus aureus* full length, N(2-29)-terminally truncated and N(1-59)-terminally truncated Sortase A:

```
full:
MKKWTNRLMT IAGVVLILVA AYLFAKPHID NYLHDKDKDE

N(2-29):
---------- ---------- --------MD NYLHDKDKDE

N(1-59):
---------- ---------- ---------- ---------- full:
KIEQYDKNVK EQASKDKKQQ AKPQIPKDKS KVAGYIEIPD

N(2-29):
KIEQYDKNVK EQASKDKKQQ AKPQIPKDKS KVAGYIEIPD

N(1-59):
---------- ---------Q AKPQIPKDKS KVAGYIEIPD full:
ADIKEPVYPG PATPEQLNRG VSFAEENESL DDQNISIAGH

N(2-29):
ADIKEPVYPG PATPEQLNRG VSFAEENESL DDQNISIAGH

N(1-59):
ADIKEPVYPG PATPEQLNRG VSFAEENESL DDQNISIAGH full:
TFIDRPNYQF TNLKAAKKGS MVYFKVGNET RKYKMTSIRD

N(2-29):
TFIDRPNYQF TNLKAAKKGS MVYFKVGNET RKYKMTSIRD

N(1-59):
TFIDRPNYQF TNLKAAKKGS MVYFKVGNET RKYKMTSIRD full:
VKPTDVGVLD EQKGKDKQLT LITCDDYNEK TGVWEKRKIF

N(2-29):
VKPTDVGVLD EQKGKDKQLT LITCDDYNEK TGVWEKRKIF

N(1-59):
VKPTDVGVLD EQKGKDKQLT LITCDDYNEK TGVWEKRKIF
full:
VATEVK
```

-continued

```
N(2-29):
VATEVK

N(1-59):
VATEVK
```

Herein is reported a novel Sortase A from *Listeria monocytogenes* with the following amino acid sequence (the catalytic center is underlined; the conserved histidine is underlined):

```
                                            (SEQ ID NO: 35)
MLKKTIAAAA LAAGLLLIFS PFIKNGIVKY MSGHETIEQY

KASDIKKNNE KDATFDFESV QLPSMTSVIK GAANYDKDAV

VGSIAVPSVD VNLLVFKGTN TANLLAGATT MRSDQVMGKG

NYPLAGHHMR DESMLFGPIM KVKKGDKIYL TDLENLYEYT

VTETKTIDET EVSVIDDTKD ARITLITCDK PTETTKRFVA

VGELEKTEKL TKELENKYFP SK.
```

In the following an alignment of *Staphylococcus aureus* Sortase A (sa-srtA) and the novel *Listeria monocytogenes* Sortase A as reported herein (lm-srtA) is shown (the catalytic center is underlined; the conserved histidine is underlined):

```
sa-srtA:
MKKWTNRLMT IAGVVLILVA AYLFAKPHID NYLHDKDKDE lm-srtA:
MLKKTIAAAA LAAGLLLIFS PFIKNGIVKY MSGHETIEQY sa-srtA:
KIEQYDKNVK EQASKDKKQQ AKPQIP---- ----KDKSKV lm-srtA:
KASDIKKNNE KDATFDFESV QLPSMTSVIK GAANYDKDAV sa-srtA:
AGYIEIPDAD IKEPVYPGPA TPEQLNRGVS FAEENESLDD lm-srtA:
VGSIAVPSVD VNLLVFKG-T NTANLLAGAT TMRSDQVMGK sa-srtA:
QNISIAGHTF IDRPNYQFTN LKAAKKGSMV YFKVGNETRK lm-srtA:
GNYPLAGHHM RD-ESMLFGP IMKVKKGDKI YLTDLENLYE sa-srtA:
YKMTSIRDVK PTDVGVLDEQ KGKDKQLTLI TCDDYNEKTG lm-srtA:
YTVTETKTID ETEVSVIDD- -TKDARITLI TCDKPTETTK sa-srtA:
VWEKRKIFVA TEVK lm-srtA:
RFVAVGELEK TEKLTKELEN KYFPSK
``` hywt: hypothetical sequence of *Listeria monocytogenes* Sortase A as published by Garandeau et al. (Infect. Immun. 70 (2002) 1382-1390; catalytic core and conserved histidine are underlined):

```
                                            (SEQ ID NO: 27)
MLKKTIAAAA LAAGLLLIFS PFIKNGIVKY MSGHETIEQY

KASDIKKNNE KDATFDFESV QLPSMTSVIK GAANYDKDAV

VGSIAVPSVD VNLLVFKGTN TANLLAGATT MRSDQVMGKG

NYPLAGHHMR DESMLFGPIM KVKKGDKIYL TDLENLYEYT

VTETKTIDET EVSVIDNTKD ARITLITCDK PTETTKRFVA

VGELEKTEKL TKELENKYFP SK
```

A: *Listeria monocytogenes* Sortase A variant A as reported herein:

```
                                            (SEQ ID NO: 36)
EKDATFDFES VQLPSMTSVI KGAANYDKDA VVGSIAVPSV

DVNLLVFKGT NTANLLAGAT TMRSDQVMGK GNYPLAGHHM

RDESMLFGPI MKVKKGDKIY LTDLENLYEY TVTETKTIDE

TEVSVIDDTK DARITLITCD KPTETTKRFV AVGELEKTEK

LTKELENKYF PSK
```

B: *Listeria monocytogenes* Sortase A variant B as reported herein:

```
                                            (SEQ ID NO: 37)
SVIKGAANYD KDAVVGSIAV PSVDVNLLVF KGTNTANLLA

GATTMRSDQV MGKGNYPLAG HHMRDESMLF GPIMKVKKGD

KIYLTDLENL YEYTVTETKT IDETEVSVID DTKDARITLI

TCDKPTETTK RFVAVGELEK TEKLTKELEN KYFPSK
```

C: *Listeria monocytogenes* Sortase A variant C as reported herein: 73597 (clean copy)

```
                                            (SEQ ID NO: 38)
ANYDKDAVVG SIAVPSVDVN LLVFKGTNTA NLLAGATTMR

SDQVMGKGNY PLAGHHMRDE SMLFGPIMKV KKGDKIYLTD

LENLYEYTVT ETKTIDETEV SVIDDTKDAR ITLITCDKPT

ETTKRFVAVG ELEKTEKLTK ELENKYFPSK
```

D: *Listeria monocytogenes* Sortase A variant D as reported herein:

```
                                            (SEQ ID NO: 39)
ANYDKDAVVG SIAVPSVDVN LLVFKGTNTA NLLAGATTMR

SDQVMGKGNY PLAGHHMRDE SMLFGPIMKV KKGDKIYLTD

LENLYEYTVT ETKTIDETEV SVIDDTKDAR ITLITCDKPT

ETTKRFVAVG ELEKTEK
```

E: *Listeria monocytogenes* Sortase A variant E as reported herein:

```
                                            (SEQ ID NO: 40)
GSIAVPSVDV NLLVFKGTNT ANLLAGATTM RSDQVMGKGN

YPLAGHHMRD ESMLFGPIMK VKKGDKIYLT DLENLYEYTV

TETKTIDETE VSVIDDTKDA RITLITCDKP TETTKRFVAV

GELEKTEKLT KELENKYFPS K
```

Alignment of the hypothetical *Listeria monocytogenes* Sortase A and the variants A to E as reported herein is shown in the following (amino acid difference is bold and underlined; the catalytic center is underlined):

```
hywt:
MLKKTIAAAA LAAGLLLIFS PFIKNGIVKY MSGHETIEQY

A:
---------- ---------- ---------- ----------

B:
---------- ---------- ---------- ----------

C:
---------- ---------- ---------- ----------

D:
---------- ---------- ---------- ----------

E:
---------- ---------- ---------- ---------- hywt:
KASDIKKNNE KDATFDFESV QLPSMTSVIK GAANYDKDAV

A:
---------E KDATFDFESV QLPSMTSVIK GAANYDKDAV

B:
---------- ---------- ------SVIK GAANYDKDAV

C:
---------- ---------- ---------- --ANYDKDAV

D:
---------- ---------- ---------- --ANYDKDAV

E:
---------- ---------- ---------- ---------- hywt:
VGSIAVPSVD VNLLVFKGTN TANLLAGATT MRSDQVMGKG

A:
VGSIAVPSVD VNLLVFKGTN TANLLAGATT MRSDQVMGKG

B:
VGSIAVPSVD VNLLVFKGTN TANLLAGATT MRSDQVMGKG

C:
VGSIAVPSVD VNLLVFKGTN TANLLAGATT MRSDQVMGKG

D:
VGSIAVPSVD VNLLVFKGTN TANLLAGATT MRSDQVMGKG

E:
-GSIAVPSVD VNLLVFKGTN TANLLAGATT MRSDQVMGKG hywt:
NYPLAGHHMR DESMLFGPIM KVKKGDKIYL TDLENLYEYT

A:
NYPLAGHHMR DESMLFGPIM KVKKGDKIYL TDLENLYEYT

B:
NYPLAGHHMR DESMLFGPIM KVKKGDKIYL TDLENLYEYT

C:
NYPLAGHHMR DESMLFGPIM KVKKGDKIYL TDLENLYEYT

D:
NYPLAGHHMR DESMLFGPIM KVKKGDKIYL TDLENLYEYT

E:
NYPLAGHHMR DESMLFGPIM KVKKGDKIYL TDLENLYEYT hywt:
VTETKTIDET EVSVIDNTKD ARITLITCDK PTETTKRFVA
```

-continued

```
A:
VTETKTIDET EVSVIDDTKD ARITLITCDK PTETTKRFVA

B:
VTETKTIDET EVSVIDDTKD ARITLITCDK PTETTKRFVA

C:
VTETKTIDET EVSVIDDTKD ARITLITCDK PTETTKRFVA

D:
VTETKTIDET EVSVIDDTKD ARITLITCDK PTETTKRFVA

E:
VTETKTIDET EVSVIDDTKD ARITLITCDK PTETTKRFVA hywt:
VGELEKTEKL TKELENKYFP SK

A:
VGELEKTEKL TKELENKYFP SK

B:
VGELEKTEKL TKELENKYFP SK

C:
VGELEKTEKL TKELENKYFP SK

D:
VGELEKTEK- ---------- --

E:
VGELEKTEKL TKELENKYFP SK
```

The herein shown different truncated versions of the novel *Listeria monocytogenes* Sortase A have different enzymatic activity.

| Listeria monocytogenes sortase variant | maximum dE/min |
|---|---|
| A | 0.037 |
| B | 0.026 |
| C | 0.113 |
| D | 0.044 |
| E | 0.019 |

The herein reported truncated version of a novel *Listeria monocytogenes* Sortase A is especially suited for in vitro bioconjugation. It recognizes a LPXTA sortase-motif and shows improved reaction kinetic properties compared to St.py. SrtA.

The herein reported truncated version of a novel *Listeria monocytogenes* Sortase A can be used as such (i.e. in isolated form) or as part of a fusion polypeptide.

In FIGS. 1 and 2 the activities of the *Listeria monocytogenes* Sortase A variant C as reported herein and the St.py. SrtA are shown.

To determine the affinity of the two sortases towards the LPKTA sortase-motif, reactions with different concentrations were analyzed. It can be seen that formation of the enzyme intermediate is the rate limiting step in the sortases mediated ligation. Therefore it was possible to perform the reactions with the nucleophile not in saturation (see e.g. Chen, I., et al., Proc. Natl. Acad. Sci. USA 108 (2011) 11399-113404). FIGS. 3 and 4 show the activity of *Listeria monocytogenes* Sortase A variant C as reported herein and St.py. SrtA with different LPKTA concentrations.

The graphs show the higher activity of *Listeria monocytogenes* Sortase A variant C and a substrate inhibition effect for St.py. SrtA at concentrations higher than 300 μM.

IV. Use of the New Sortase as Reported Herein One aspect as reported herein is a method for the enzymatic production of a polypeptide comprising the following step
incubating
i) a first polypeptide comprising (optionally within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
ii) a second polypeptide that has i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and
iii) a polypeptide as reported herein,
and thereby producing a polypeptide.

In one embodiment the method is for the enzymatic conjugation of two polypeptides.

In one embodiment the second polypeptide has at its N-terminus the amino acid sequence GGG, AAA, CGG, CAA, KGG, or KAA.

In one embodiment the polypeptide as reported herein comprises the amino acid sequence of SEQ ID NO: 38 or is a (fusion) polypeptide comprising one domain that has the amino acid sequence of SEQ ID NO: 38 and one or more further domains, wherein the domain that has the amino acid sequence of SEQ ID NO: 38 and any of the further domains are from polypeptides from different organisms, wherein the domains are conjugated to each other either directly or via a peptidic linker.

In one embodiment the first polypeptide comprises within the 250 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 100 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 25 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 10 C-terminal amino acid residues the amino acid sequence LPXTG (SEQ ID NO: 01, wherein X can be any amino acid residue) or LPXTA (SEQ ID NO: 41, wherein X can be any amino acid residue).

In one embodiment the first polypeptide comprises at its C-terminus the amino acid sequence LPXTG (SEQ ID NO: 01, wherein X can be any amino acid residue) or LPXTA (SEQ ID NO: 41, wherein X can be any amino acid residue). In one embodiment the first polypeptide comprises at its C-terminus the amino acid sequence LPETG (SEQ ID NO: 04) or LPETA (SEQ ID NO: 42) or LPKTG (SEQ ID NO: 43) or LPKTA (SEQ ID NO: 44).

In one embodiment the first polypeptide and the second polypeptide are independently of each other selected from an antibody variable domain, an antibody heavy chain Fab-fragment, an antibody Fc-region, a tag, and a peptide, a linker and a non-sortase motif moiety, whereby the first polypeptide comprises the amino acid sequence LPXTG (SEQ ID NO: 01, wherein X can be any amino acid residue) or LPXTA (SEQ ID NO: 41, wherein X can be any amino acid residue).

The First or Second Polypeptide

The sortase-motif (amino acid sequence) may be conjugated to or incorporated in, if it is not directly comprised in one of these molecules, a therapeutic agent (drug), a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label, a tag, or a clearance-modifying agent such as various isomers of polyethylene glycol, a peptide that binds to a third component, another carbohydrate or lipophilic agent, or a small molecule, such as e.g. a synthetic small molecule (e.g. acetyl salicylic acid). If the motif is incorporated via conjugation the conjugation can be either directly or via an intervening linker. Furthermore the first and/or second polypeptide can either be recombinantly produced or can be synthetic or semi-synthetic, i.e. recombinantly produced and thereafter chemically modified.

a) Therapeutic Agents

The therapeutic agent can be any compound, moiety or group which has a therapeutic effect, such as e.g. an antibody, a cytotoxic or cytostatic compound. The antibody can be a full length or complete antibody or an antigen-binding fragment thereof.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of a431 and a4B7 integrins), ReoPro/Abciximab (gpIIb-gpIIa and αvß3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CDS, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RS5, RANTES, T101, SAGE, S100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-IA-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multispecific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. Nos. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544); and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL 6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T lymphocytes NK cell, B-lymphocytes, dendritic cells, monocytes, macrophages, neutrophils, mesenchymal stem cells, neural stem cells, ANG2/VEGF, VEGF/PDGFR-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PlGF, PDGF, HGF, and angiopoietin, ERBB-3/C-MET, ERBB-2/C-MET, EGF receptor 1/CD3, EGFR/ER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alphasarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The non-sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & IT Van Vunakis), Academic Press, New York, 73 (1981) 147-166.

Examples of enzyme-substrate combinations (U.S. Pat. Nos. 4,275,149; 4,318,980) include, for example:
(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));
(ii) alkaline phosphatase (AP) with para-nitrophenyl phosphate as chromogenic substrate; and
(iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tscheshe, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

c) Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, and alpha-haloacetyl.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or 3-amino acids, such as e.g. β-alanine, or co-amino acids such as 4-aminobutyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E.

Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate (S03-) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)3, and BM(PEO)4, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys (Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, hydrazine carboxylate, and arylhydrazide groups capable of reacting to form covalent bonds with electrophilic groups on linker moieties and linker reagents.

V. Recombinant Methods

Any polypeptide domain (e.g. a single chain antigen binding polypeptide such as a scFv, a scFab, or a darpin, or a multi chain antigen binding polypeptide such as a dsFv or a Fab) comprising an nucleophilic amino acid sequence at its N-terminus, such as e.g. an oligoglycine motif (GG (SEQ ID NO: 28), GGG (SEQ ID NO: 29), GGGG (SEQ ID NO: 30), GGGGG (SEQ ID NO: 31)), can be expressed und purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B.K.C. Lo, (ed.), Humana Press, Totowa, N.J.), describing expression of antibody fragments in E. coli.). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRC5 cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B.K.C. Lo, (ed.), Humana Press, Totowa, N.J.).

DESCRIPTION OF THE FIGURES

FIG. 2 0.67 mg/ml of Listeria monocytogenes SrtA variant C (diamond) and St.py. SrtA (square) were incubated for different hours with 92 µM glucose Dehydrogenase harboring a LPKTA motive and 7 µM AAAA-biotin and 7 µM GGGG-biotin. After incubation on the Streptavidin beads, 10 µl of the suspension where analyzed for the reporter enzyme activity.

FIG. 3 1 mg/ml of *Listeria monocytogenes* SrtA variant C was incubated for 2 h with different concentrations of glucose Dehydrogenase harboring a LPKTA motive and 14 µM GGGG-Biotin. After incubation on the Streptavidin beads 40 µl of the suspension where analyzed for the reporter enzyme activity.

FIG. 4 3 mg/ml of St.py. SrtA was incubated for 2 h with different concentrations of Glucose Dehydrogenase harboring a LPKTA motive and 14 µM GGGG-Biotin. After incubation on the streptavidin beads, 40 µl of the suspension where analyzed for the reporter enzyme activity.

Figure 1:
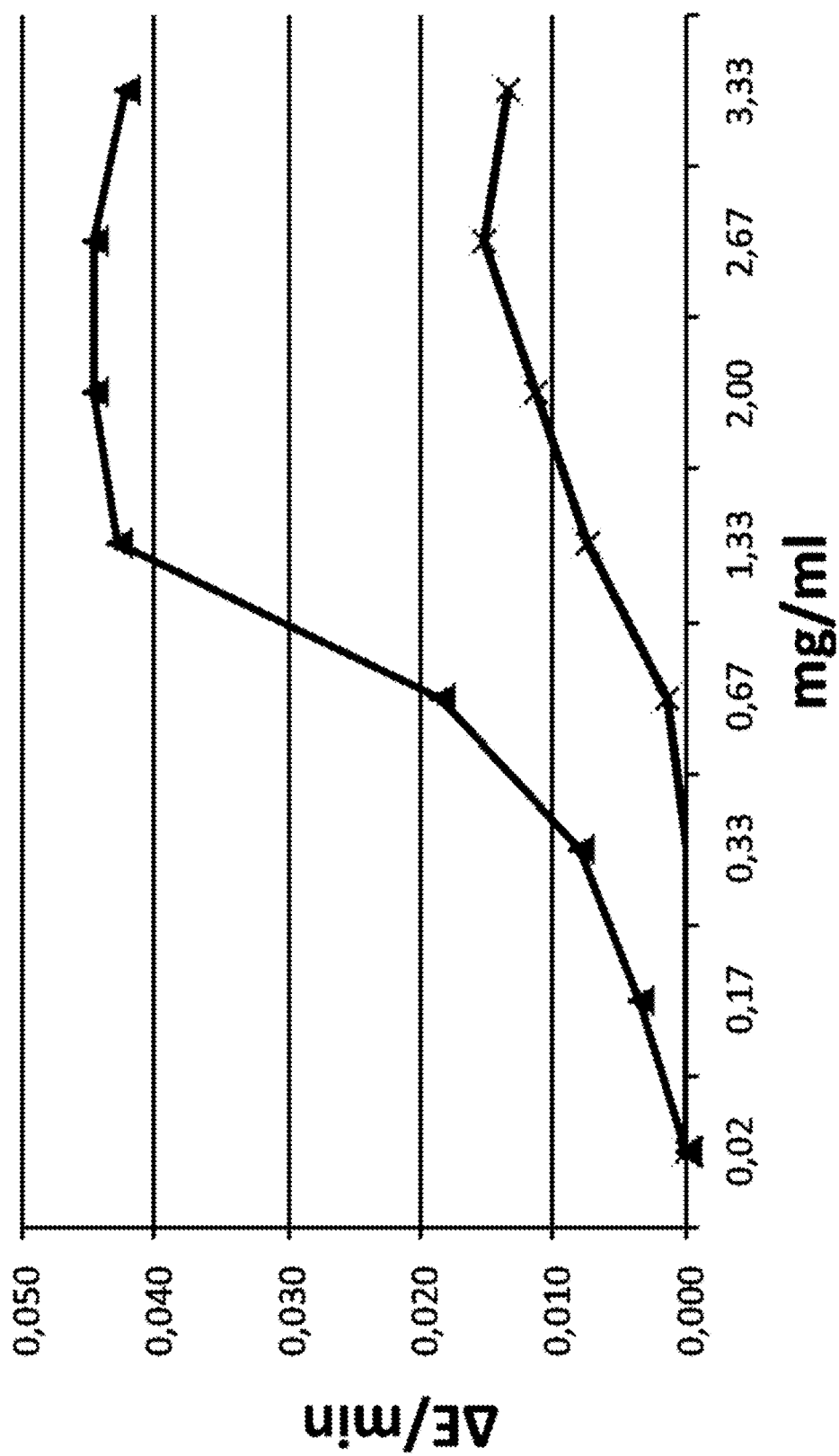
FIG. 1 Different concentrations of Listeria monocytogenes Sortase A variant C (triangles) and St.py. SrtA (crosses) were incubated for 2h with 92 µM glucose Dehydrogenase harboring a LPKTA motive and 7 µM AAAA-biotin and 7 M GGGG-biotin. After incubation on the Streptavidin beads, 10 µl of the suspension where analyzed for the reporter enzyme activity.

The following examples, figures and sequences are provided to aid the understanding of the present invention, the true scope of which is set forth in the appended claims. It is understood that modifications can be made in the procedures set forth without departing from the spirit of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
  the immediate early enhancer and promoter from the human cytomegalovirus (P-CMV) including intron A,
  a human heavy chain immunoglobulin 5'-untranslated region (5'UTR),
  a murine immunoglobulin heavy chain signal sequence,
  a gene/protein to be expressed (e.g. full length antibody heavy chain), and
  the bovine growth hormone polyadenylation sequence (BGH pA).

Beside the expression unit/cassette including the desired gene to be expressed the basic/standard mammalian expression plasmid contains
  an origin of replication from the vector pUC18 which allows replication of this plasmid in *E. coli*, and
  a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Soluble Sortase A

*Staphylococcus aureus* derived Sortase A The sortase gene encodes an N-terminally truncated *Staphylococcus aureus* sortase A (60-206) molecule (amino acid sequence of SEQ ID NO: 05).

The expression plasmid for the expression of soluble sortase in *E. coli* cells comprised besides the soluble sortase expression cassette an origin of replication from the vector pUC18, which allows replication of this plasmid in *E. coli*, and the URA3 gene as selectable marker, and the LacI gene to allow induction of transcription using IPTG.

The transcription unit of the soluble sortase comprised the following functional elements:
  a T5 promoter,
  a purification tag,
  an N-terminally truncated *S. aureus* sortase A encoding nucleic acid, and
  the To and fd termination sequences.

The expression plasmid for the transient expression of soluble sortase in HEK293 cells comprised besides the soluble sortase expression cassette an origin of replication from the vector pUC18, which allows replication of this plasmid in *E. coli*, and a beta-lactamase gene which confers ampicillin resistance in *E. coli*.

The transcription unit of the soluble sortase comprised the following functional elements:
  the immediate early enhancer and promoter from the human cytomegalovirus (P-CMV) including intron A,
  a human heavy chain immunoglobulin 5'-untranslated region (5'UTR),
  a murine immunoglobulin heavy chain signal sequence,
  a purification tag encoding nucleic acid,
  an N-terminally truncated *S. aureus* sortase A encoding nucleic acid, and
  the bovine growth hormone polyadenylation sequence (BGH pA).

The amino acid sequence of the mature soluble sortase is (SEQ ID NO: 05)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVK.

The purification tag has the amino acid sequence MRGSHHHHHHGS (SEQ ID NO: 32).

*Streptococcus pyogenes* Derived Sortase A

The sortase gene encodes an N-terminally truncated *Streptococcus pyogenes* sortase A molecule (amino acid sequence of SEQ ID NO: 06).

The expression plasmid for the expression of soluble sortase in *E. coli* cells comprised besides the soluble sortase expression cassette an origin of replication from the vector pUC18, which allows replication of this plasmid in *E. coli*, and the URA3 gene as selectable marker, and the LacI gene to allow induction of transcription using IPTG.

The transcription unit of the soluble sortase comprised the following functional elements:

a T5 promoter, a purification tag, an N-terminally truncated *S. pyogenes* sortase A encoding nucleic acid, and the To and fd termination sequences.

The expression plasmid for the transient expression of soluble sortase in HEK293 cells comprised besides the soluble sortase expression cassette an origin of replication from the vector pUC18, which allows replication of this plasmid in *E. coli*, and a beta-lactamase gene which confers ampicillin resistance in *E. coli*.

The transcription unit of the soluble sortase comprised the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, a purification tag encoding nucleic acid, an N-terminally truncated *S. pyogenes* sortase A encoding nucleic acid, and the bovine growth hormone polyadenylation sequence (BGH pA).

The amino acid sequence of the mature soluble sortase is (SEQ ID NO: 06)
VLQAQMAAQQLPVIGGIAIPELGINLPIFKGLGNTELIYGAGTMKEEQVM

GGENNYSLASHHIFGITGSSQMLFSPLERAQNGMSIYLTDKEKIYEYIIK

DVFTVAPERVDVIDDTAGLKEVTLVTCTDIEATERIIVKGELKTEYDFDK

APADVLKAFNHSYNQVST.

The purification tag has the amino acid sequence MRGSHHHHHHGS (SEQ ID NO: 32).

*Listeria monocytogenes* Derived Sortase A

Different sortase genes encoding N-terminally truncated *Listeria monocytogenes* sortase A molecules were expressed:

A: *Listeria monocytogenes* Sortase A variant A as reported herein:

(SEQ ID NO: 36)
EKDATFDFESVQLPSMTSVIKGAANYDKDAVVGSIAVPSVDVNLLVFKGT

NTANLLAGATTMRSDQVMGKGNYPLAGHHMRDESMLFGPIMKVKKGDK

IYLTDLENLYEYTVTETKTIDETEVSVIDDTKDARITLITCDKPTETTKR

FVAVGELEKTEKLTKELENKYFPSK

B: *Listeria monocytogenes* Sortase A variant B as reported herein:

(SEQ ID NO: 37)
SVIKGAANYDKDAVVGSIAVPSVDVNLLVFKGTNTANLLAGATTMRSDQ

VMGKGNYPLAGHHMRDESMLFGPIMKVKKGDKIYLTDLENLYEYTVTET

KTIDETEVSVIDDTKDARITLITCDKPTETTKRFVAVGELEKTEKLTKEL

ENKYFPSK

C: *Listeria monocytogenes* Sortase A variant C as reported herein:

(SEQ ID NO: 38)
ANYDKDAVVGSIAVPSVDVNLLVFKGTNTANLLAGATTMRSDQVMGKG

NYPLAGHHMRDESMLFGPIMKVKKGDKIYLTDLENLYEYTVTETKTIDET

EVSVIDDTKDARITLITCDKPTETTKRFVAVGELEKTEKLTKELENKYFP

SK

D: *Listeria monocytogenes* Sortase A variant D as reported herein:

(SEQ ID NO: 39)
ANYDKDAVVGSIAVPSVDVNLLVFKGTNTANLLAGATTMRSDQVMGKG

NYPLAGHHMRDESMLFGPIMKVKKGDKIYLTDLENLYEYTVTETKTIDET

EVSVIDDTKDARITLITCDKPTETTKRFVAVGELEKTEK

E: *Listeria monocytogenes* Sortase A variant E as reported herein:

(SEQ ID NO: 40)
GSIAVPSVDVNLLVFKGTNTANLLAGATTMRSDQVMGKGNYPLAGHHMR

DESMLFGPIMKVKKGDKIYLTDLENLYEYTVTETKTIDETEVSVIDDTKD

ARITLITCDKPTETTKRFVAVGELEKTEKLTKELENKYFPSK

The expression plasmid for the expression of the truncated sortases in *E. coli* cells comprised besides the sortase expression cassette an origin of replication from the vector pUC18, which allows replication of this plasmid in *E. coli*, and the URA3 gene as selectable marker, and the LacI gene to allow induction of transcription using IPTG.

The transcription unit of the soluble sortase comprised the following functional elements:

a T5 promoter, a purification tag, the *Listeria monocytogenes* sortase A variant encoding nucleic acid, and the To and fd termination sequences.

The expression plasmid for the transient expression of truncated sortases in HEK293 cells comprised besides the sortase expression cassette an origin of replication from the vector pUC18, which allows replication of this plasmid in *E. coli*, and a beta-lactamase gene which confers ampicillin resistance in *E. coli*.

The transcription unit of the soluble sortase comprised the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, a purification tag encoding nucleic acid, the *L. monocytogenes* sortase A variant encoding nucleic acid, and the bovine growth hormone polyadenylation sequence (BGH pA).

The purification tag has the amino acid sequence MRGSHHHHHHGS (SEQ ID NO: 32).

Example 2

Transient Expression and Analytical Characterization
E. coli:

The recombinant production of Sortase was performed by growing E. coli cells transformed with the respective Sortase expression plasmids to an OD578 of approx. 0.9 at 37° C. (pre-culture). At this OD578 of approx. 0.9 protein expression was induced by adding 2 mM IPTG and growing the cells for an additional 24 hours at 28° C. Thereafter, cells were harvested by centrifugation and lysed via high pressure using a homogenizer. Cell lysates were centrifuged to remove cell debris and subsequently the cell lysates were stored at reduced temperature (e.g. −80° C.) until purification. Soluble Sortase was purified using Ni-NTA chromatography followed by size exclusion chromatography. For depletion of endotoxins an anion exchange chromatography was performed in flow through mode. The protein concentration of sortase preparations was determined by measuring the optical density (OD) at 280 nm, using the molar extinction coefficient calculated on the basis of the amino acid sequence. Purity and integrity of sortase was determined by SDS-PAGE in the presence and absence of a reducing agent (5 mM 1,4-dithiotreitol) and staining with Coomassie brilliant blue.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

HEK:

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

The Listeria monocytogenes Sortase A variant D showed very low expression yields.

Example 3

Activity Assay

Forty microliters of each variant were mixed with 80 µl substrate solution (50 mM Tris pH 7.5, 200 mM NaCl, 10 mM CaCl$_2$, 30 µM of a glucose dehydrogenase (containing one of the substrates of the Sortase reaction (LPXTG)) and biotin (containing the other substrate of the Sortase reaction, GGGG)). This reaction mixture was incubated at 37° C. for 2 hours. Thereafter the reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and streptavidin coated magnetic beads. The mixture was incubated for 30 min at 30° C. at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom micro-titer-plates using a magnet and a vacuum pump. Afterwards the beads were resuspended in 100 µL citrate buffer and 10 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

The activity of the different variants is shown in the following Table.

| Listeria monocytogenes sortase variant | maximum dE/min |
|---|---|
| A (SEQ ID NO: 36 + C-terminal SEQ ID NO: 32) | 0.037 |
| B (SEQ ID NO: 37 + C-terminal SEQ ID NO: 32) | 0.026 |
| C (SEQ ID NO: 38 + C-terminal SEQ ID NO: 32) | 0.113 |
| D (SEQ ID NO: 39 + C-terminal SEQ ID NO: 32) | 0.044 |
| E (SEQ ID NO: 40 + C-terminal SEQ ID NO: 32) | 0.019 |

Example 4

Kinetic Assays
Enzyme Amount

Different concentrations of Sortase (0.02 mg/ml, 0.17 mg/ml, 0.33 mg/ml, 0.67 mg/ml, 1.33 mg/ml, 2.00 mg/ml, 2.67 mg/ml, 3.33 mg/ml) were mixed with substrate solution (50 mM Tris pH 7.5, 200 mM NaCl, 10 mM CaCl$_2$, 92 µM glucose dehydrogenase (containing one of the substrates of the Sortase reaction (LPKTA) and 7 µM biotin (containing the other substrate of the Sortase reaction, AAAA) and 7 µM biotin (containing the other substrate of the Sortase reaction, GGGG)). This reaction mixture was incubated at 37° C. for 2 hours. The reaction was stopped by addition of a 20-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and Streptavidin coated magnetic beads. The mixture was incubated for 30 min at 30° C. at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom multi-well plates using a magnet and a vacuum pump. Afterwards the beads were resuspended in 100 µL citrate buffer and 10 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

The activity of the St.py. SrtA and Listeria monocytogenes Sortase A variant C are shown in FIG. 1.

Incubation Time

A fixed concentrations of Sortase (0.67 mg/ml) were mixed with substrate solution (50 mM Tris pH 7.5, 200 mM NaCl, 10 mM CaCl$_2$, 92 µM glucose dehydrogenase (containing one of the substrates of the Sortase reaction (LPKTA) and 7 µM biotin (containing the other substrate of the Sortase reaction, AAAA) and 7 µM biotin (containing the other substrate of the Sortase reaction, GGGG)). This reaction mixture was incubated at 37° C. for 2, 6.5 or 18 hours. The reaction was stopped by addition of a 20-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and Streptavidin coated magnetic beads. The mixture was incubated for 30 min at 30° C. at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom multi-well plates using a magnet and a vacuum pump. Afterwards the beads were resuspended in 100 µL citrate buffer and 10 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

Figure 2:
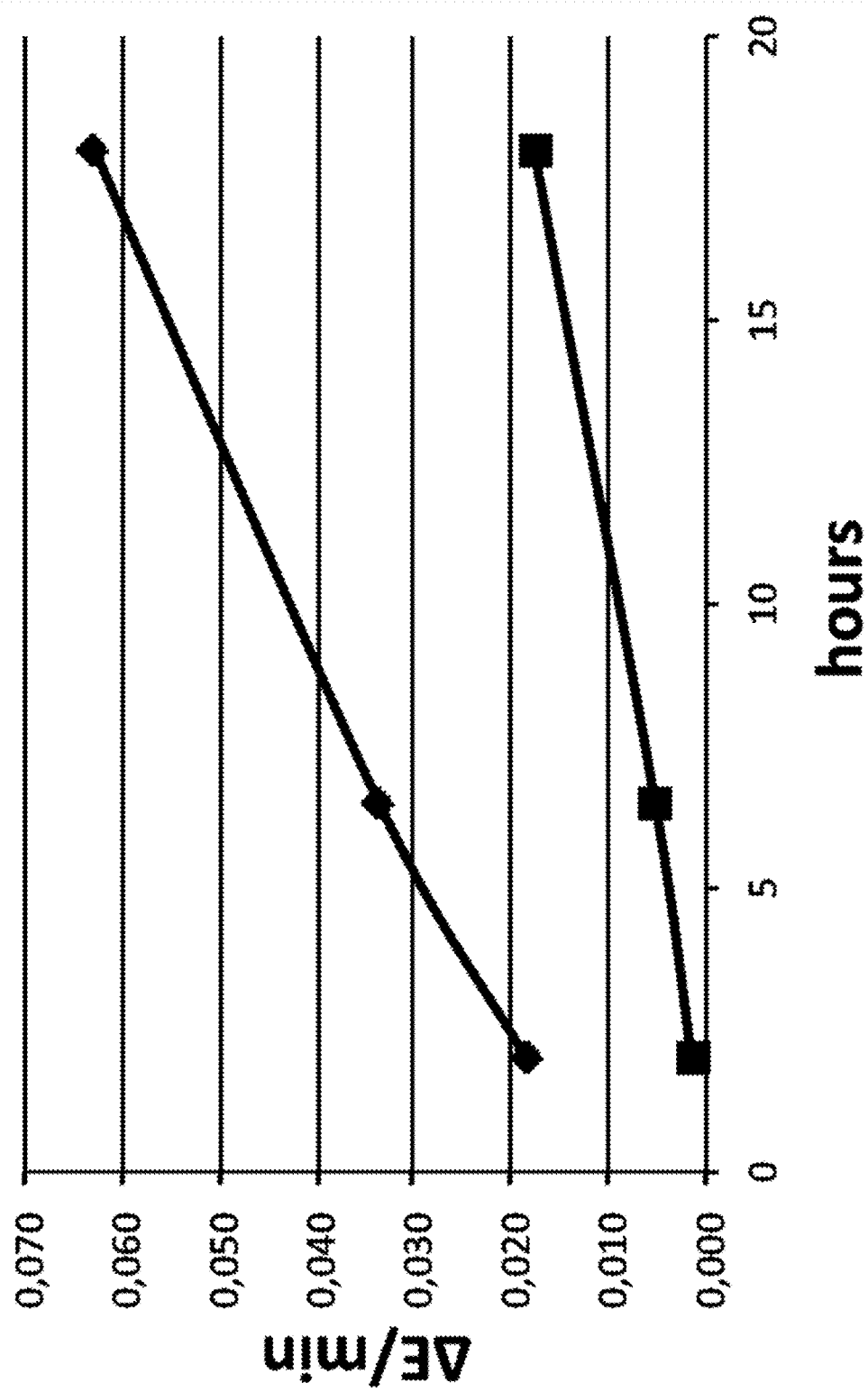

The activity of the St.py. SrtA and *Listeria monocytogenes* Sortase A variant C are shown in FIG. 2.

Sortase-Motif Polypeptide Concentration

A fixed concentrations of *Listeria monocytogenes* Sortase variant C (1 mg/ml) were mixed with substrate solution (50 mM Tris pH 7.5, 200 mM NaCl, 10 mM CaCl$_2$, 2.5, 5, 10, 20, 40, 80, 160, 325, 650, 1300 µM glucose dehydrogenase (containing one of the substrates of the Sortase reaction (LPKTA) and 14 µM biotin (containing the other substrate of the Sortase reaction, GGGG)). This reaction mixture was incubated at 37° C. for 2 hours. The reaction was stopped by addition of a 20-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and Streptavidin coated magnetic beads. The mixture was incubated for 30 min at 30° C. at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom multi-well plates using a magnet and a vacuum pump. Afterwards the beads were resuspended in 100 µL citrate buffer and 40 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

Figure 3:
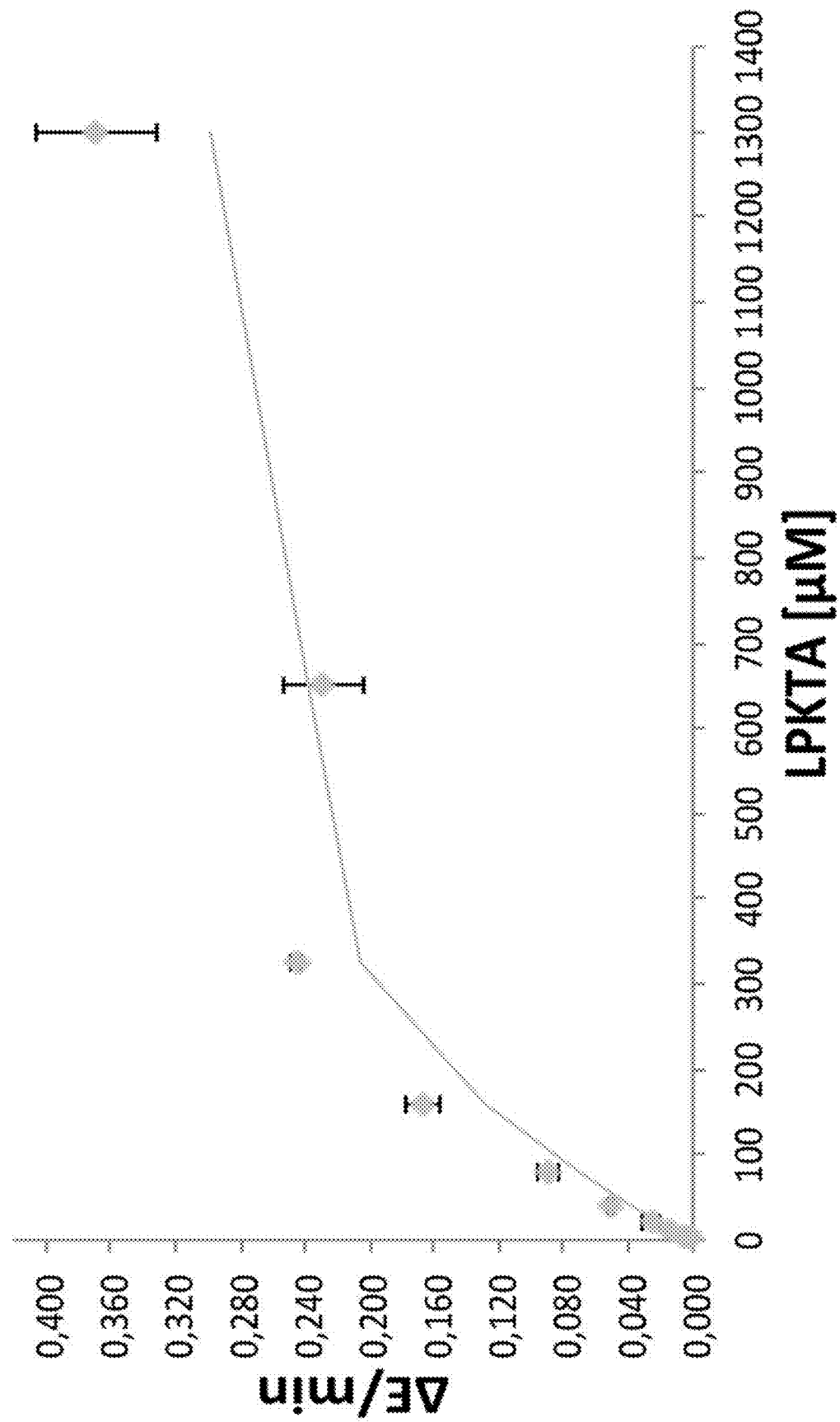

The activity of the *Listeria monocytogenes* Sortase A variant C is shown in FIG. 3.

Sortase-Motif Polypeptide Concentration

A fixed concentrations of *Staphylococcus pyogenes* Sortase (3 mg/ml) were mixed with substrate solution (50 mM Tris pH 7.5, 200 mM NaCl, 10 mM CaCl$_2$, 2.5, 5, 10, 20, 40, 80, 160, 325, 650, 1300 µM glucose dehydrogenase (containing one of the substrates of the Sortase reaction (LPKTA) and 14 µM biotin (containing the other substrate of the Sortase reaction, GGGG)). This reaction mixture was incubated at 37° C. for 2 hours. The reaction was stopped by addition of a 20-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and Streptavidin coated magnetic beads. The mixture was incubated for 30 min at 30° C. at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom multi-well plates using a magnet and a vacuum pump. Afterwards the beads were resuspended in 100 µL citrate buffer and 40 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

Figure 4:
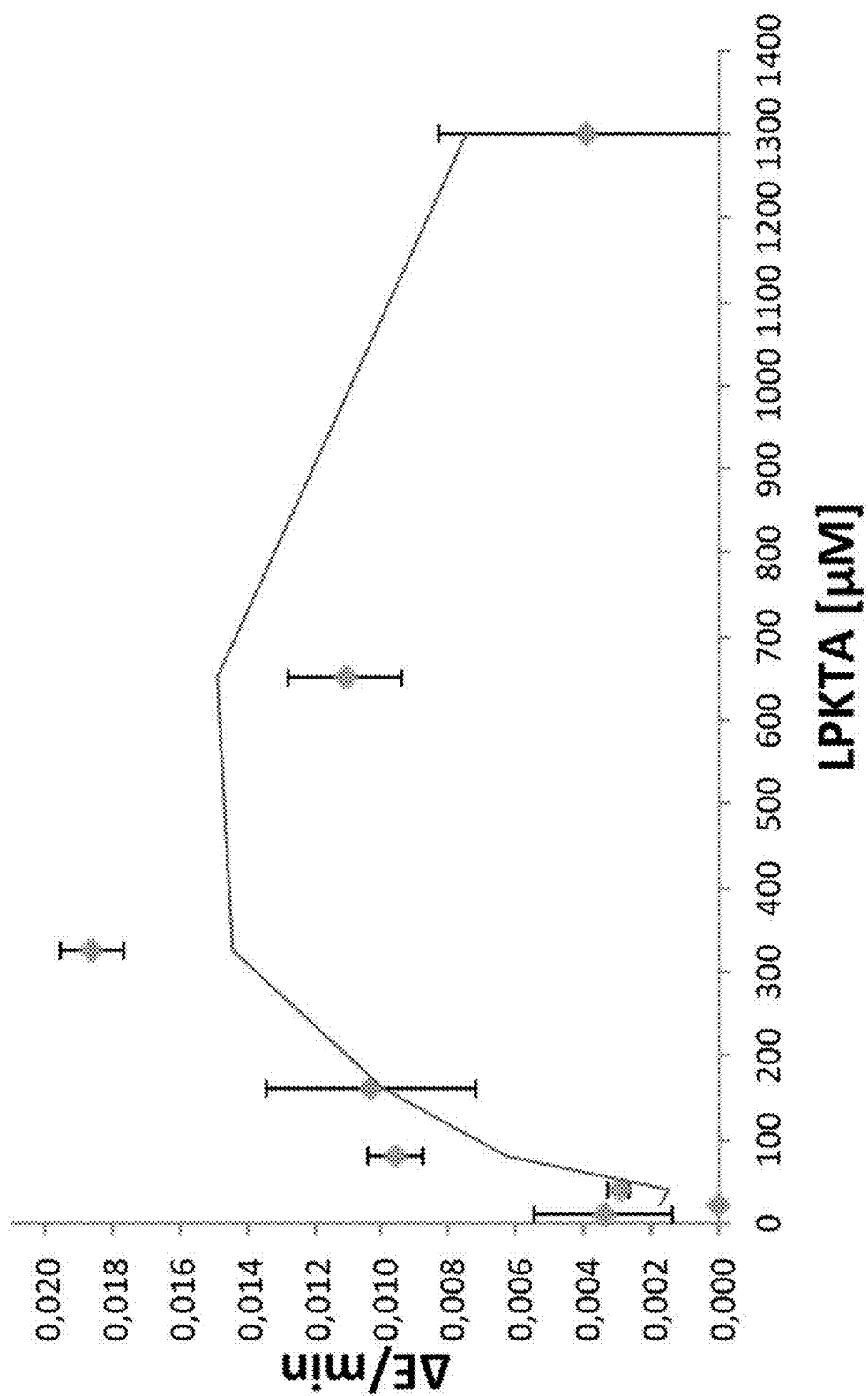

The activity of the *Streptococcus pyogenes* Sortase A is shown in FIG. 4.

Although the foregoing invention has been described in some detail by way of illustration and example for purposes of clarity of understanding, the descriptions and examples should not be construed as limiting the scope of the invention.

The invention claimed is:

1. A non-native polypeptide consisting of SEQ ID NO: 38.

2. A method for conjugating two polypeptides comprising the step of incubating in an aqueous environment the polypeptide according to claim 1 with
   a first polypeptide comprising a sortase-motif comprising the amino acid sequence LPXTG (SEQ ID NO: 01, wherein X can be any amino acid residue) or LPXTA (SEQ ID NO: 41, wherein X can be any amino acid residue), and
   a second polypeptide comprising an oligoglycine or oligoalanine or a cysteine amino acid residue followed by one to three glycine or alanine amino acid residues at its N-terminus.

3. A method for enzymatically producing a polypeptide comprising the following step
   incubating in an aqueous environment
   i) a first polypeptide comprising the amino acid sequence LPXTG (SEQ ID NO: 01, wherein X can be any amino acid residue) or LPXTA (SEQ ID NO: 41, wherein X can be any amino acid residue),
   ii) a second polypeptide that comprises i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or
   iii) a lysine amino acid residue within its 5 N-terminal amino acid residues, and
   iii) the polypeptide according to claim 1;
   thereby producing a polypeptide.

4. The method according to claim 3, wherein the second polypeptide has at its N-terminus the amino acid sequence GGG, AAA, CGG, CAA, KGG or KAA.

5. The method according to claim 3, wherein the first polypeptide comprises at its C-terminus the amino acid sequence LPXTG (SEQ ID NO: 01, wherein X can be any amino acid residue) or LPXTA (SEQ ID NO: 41, wherein X can be any amino acid residue).

6. The method according to claim 3 wherein the first polypeptide comprises at its C-terminus the amino acid sequence LPETG (SEQ ID NO: 04) or LPETA (SEQ ID NO: 42).

7. The method according to claim 3, wherein the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 01, wherein X can be any amino acid residue) or LPXTA (SEQ ID NO: 41, wherein X can be any amino acid residue), a linker and a non-sortase motif moiety.

* * * * *

SEQUENCE LISTING

```
<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
<223> OTHER INFORMATION: LPXTG sortase-motif
<220> FEATURE:
<221> NAME/KEY: MISC_FEATURE
<222> LOCATION: (3)..(3)
<223> OTHER INFORMATION: X can be any amino acid residue

<400> SEQUENCE: 1

Leu Pro Xaa Thr Gly
1               5

<210> SEQ ID NO 2
<211> LENGTH: 4
<212> TYPE: PRT
<213> ORGANISM: Artificial Sequence
<220> FEATURE:
<223> OTHER INFORMATION: cystein sortase motif 1

<400> SEQUENCE: 2
```

```
Cys Gly Gly Gly
1
```

<210> SEQ ID NO 3
<211> LENGTH: 4
<212> TYPE: PRT
<213> ORGANISM: Artificial Sequence
<220> FEATURE:
<223> OTHER INFORMATION: cystein sortase motif 2

<400> SEQUENCE: 3

```
Cys Ala Ala Ala
1
```

<210> SEQ ID NO 4
<211> LENGTH: 5
<212> TYPE: PRT
<213> ORGANISM: Artificial Sequence
<220> FEATURE:
<223> OTHER INFORMATION: sortase motif

<400> SEQUENCE: 4

```
Leu Pro Glu Thr Gly
1               5
```

<210> SEQ ID NO 5
<211> LENGTH: 147
<212> TYPE: PRT
<213> ORGANISM: Artificial Sequence
<220> FEATURE:
<223> OTHER INFORMATION: Staphylococcus aureus Sortase A shortened
      version N(1-59)

<400> SEQUENCE: 5

```
Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys
145
```

<210> SEQ ID NO 6
<211> LENGTH: 168
<212> TYPE: PRT
<213> ORGANISM: Artificial Sequence
<220> FEATURE:
<223> OTHER INFORMATION: Streptococcus pyogenes Sortase A shortened
      version

```
<400> SEQUENCE: 6

Val Leu Gln Ala Gln Met Ala Ala Gln Leu Pro Val Ile Gly Gly
1               5                   10                  15

Ile Ala Ile Pro Glu Leu Gly Ile Asn Leu Pro Ile Phe Lys Gly Leu
                20                  25                  30

Gly Asn Thr Glu Leu Ile Tyr Gly Ala Gly Thr Met Lys Glu Glu Gln
                35                  40                  45

Val Met Gly Gly Glu Asn Asn Tyr Ser Leu Ala Ser His His Ile Phe
    50                  55                  60

Gly Ile Thr Gly Ser Ser Gln Met Leu Phe Ser Pro Leu Glu Arg Ala
65                  70                  75                  80

Gln Asn Gly Met Ser Ile Tyr Leu Thr Asp Lys Glu Lys Ile Tyr Glu
                85                  90                  95

Tyr Ile Ile Lys Asp Val Phe Thr Val Ala Pro Glu Arg Val Asp Val
                100                 105                 110

Ile Asp Asp Thr Ala Gly Leu Lys Glu Val Thr Leu Val Thr Cys Thr
                115                 120                 125

Asp Ile Glu Ala Thr Glu Arg Ile Ile Val Lys Gly Glu Leu Lys Thr
            130                 135                 140

Glu Tyr Asp Phe Asp Lys Ala Pro Ala Asp Val Leu Lys Ala Phe Asn
145                 150                 155                 160

His Ser Tyr Asn Gln Val Ser Thr
                165

<210> SEQ ID NO 7
<211> LENGTH: 5
<212> TYPE: PRT
<213> ORGANISM: Artificial Sequence
<220> FEATURE:
<223> OTHER INFORMATION: Arg-tag

<400> SEQUENCE: 7

Arg Arg Arg Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Arg-tag 2

<400> SEQUENCE: 8

Arg Arg Arg Arg Arg Arg
1               5

<210> SEQ ID NO 9
<211> LENGTH: 6
<212> TYPE: PRT
<213> ORGANISM: Artificial Sequence
<220> FEATURE:
<223> OTHER INFORMATION: His-tag

<400> SEQUENCE: 9

His His His His His His
1               5

<210> SEQ ID NO 10
<211> LENGTH: 19
<212> TYPE: PRT
<213> ORGANISM: Artificial Sequence
```

```
<220> FEATURE:
<223> OTHER INFORMATION: amino acid tag

<400> SEQUENCE: 10

Lys Asp His Leu Ile His Asn Val His Lys Glu Phe His Ala His Ala
1               5                   10                  15

His Asn Lys

<210> SEQ ID NO 11
<211> LENGTH: 8
<212> TYPE: PRT
<213> ORGANISM: Artificial Sequence
<220> FEATURE:
<223> OTHER INFORMATION: amino acid tag

<400> SEQUENCE: 11

Asp Tyr Lys Asp Asp Asp Asp Lys
1               5

<210> SEQ ID NO 12
<211> LENGTH: 22
<212> TYPE: PRT
<213> ORGANISM: Artificial Sequence
<220> FEATURE:
<223> OTHER INFORMATION: amino acid tag

<400> SEQUENCE: 12

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 13
<211> LENGTH: 9
<212> TYPE: PRT
<213> ORGANISM: Artificial Sequence
<220> FEATURE:
<223> OTHER INFORMATION: amino acid tag#

<400> SEQUENCE: 13

Ala Trp Arg His Pro Gln Phe Gly Gly
1               5

<210> SEQ ID NO 14
<211> LENGTH: 8
<212> TYPE: PRT
<213> ORGANISM: Artificial Sequence
<220> FEATURE:
<223> OTHER INFORMATION: amino acid tag

<400> SEQUENCE: 14

Trp Ser His Pro Gln Phe Glu Lys
1               5

<210> SEQ ID NO 15
<211> LENGTH: 10
<212> TYPE: PRT
<213> ORGANISM: Artificial Sequence
<220> FEATURE:
<223> OTHER INFORMATION: amino acid tag

<400> SEQUENCE: 15

Met Asp Val Glu Ala Trp Leu Gly Ala Arg
1               5                   10
```

```
<210> SEQ ID NO 16
<211> LENGTH: 16
<212> TYPE: PRT
<213> ORGANISM: Artificial Sequence
<220> FEATURE:
<223> OTHER INFORMATION: amino acid tag

<400> SEQUENCE: 16

Met Asp Val Glu Ala Trp Leu Gly Ala Arg Val Pro Leu Val Glu Thr
1               5                   10                  15

<210> SEQ ID NO 17
<211> LENGTH: 38
<212> TYPE: PRT
<213> ORGANISM: Artificial Sequence
<220> FEATURE:
<223> OTHER INFORMATION: amino acid tag

<400> SEQUENCE: 17

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 18
<211> LENGTH: 10
<212> TYPE: PRT
<213> ORGANISM: Artificial Sequence
<220> FEATURE:
<223> OTHER INFORMATION: amino acid tag

<400> SEQUENCE: 18

Glu Gln Lys Leu Ile Ser Glu Glu Asp Leu
1               5                   10

<210> SEQ ID NO 19
<211> LENGTH: 15
<212> TYPE: PRT
<213> ORGANISM: Artificial Sequence
<220> FEATURE:
<223> OTHER INFORMATION: amino acid tag

<400> SEQUENCE: 19

Lys Glu Thr Ala Ala Ala Lys Phe Glu Arg Gln His Met Asp Ser
1               5                   10                  15

<210> SEQ ID NO 20
<211> LENGTH: 26
<212> TYPE: PRT
<213> ORGANISM: Artificial Sequence
<220> FEATURE:
<223> OTHER INFORMATION: amino acid tag

<400> SEQUENCE: 20

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 21
<211> LENGTH: 47
<212> TYPE: PRT
<213> ORGANISM: Artificial Sequence
<220> FEATURE:
```

<223> OTHER INFORMATION: amino acid tag

<400> SEQUENCE: 21

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 22
<211> LENGTH: 32
<212> TYPE: PRT
<213> ORGANISM: Butyrivibrio fibrisolvens

<400> SEQUENCE: 22

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 23
<211> LENGTH: 51
<212> TYPE: PRT
<213> ORGANISM: Artificial Sequence
<220> FEATURE:
<223> OTHER INFORMATION: chitin-binding-domain

<400> SEQUENCE: 23

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 24
<211> LENGTH: 209
<212> TYPE: PRT
<213> ORGANISM: Chondrus crispus

<400> SEQUENCE: 24

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Gly Val Ile Asp
                85                  90                  95

Asp Val Thr His Ala Met Tyr Arg Tyr Arg Gly Asp Asp Lys Asp Lys
            100                 105                 110

Leu Arg Glu Glu Arg Asp Lys Phe Ser Lys Val Asp Val Pro Arg Tyr

```
            115                 120                 125
Val Gly Ala Leu Glu Lys Arg Leu Glu Ala Phe Gly Asp Gly Pro Trp
        130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205

Ser

<210> SEQ ID NO 25
<211> LENGTH: 396
<212> TYPE: PRT
<213> ORGANISM: Escherichia coli

<400> SEQUENCE: 25

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
```

```
                275                 280                 285
Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
370                 375                 380

Glu Ala Leu Lys Asp Ala Gln Thr Arg Ile Thr Lys
385                 390                 395
```

<210> SEQ ID NO 26
<211> LENGTH: 206
<212> TYPE: PRT
<213> ORGANISM: Staphylococcus aureus

<400> SEQUENCE: 26

```
Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205
```

<210> SEQ ID NO 27
<211> LENGTH: 222
<212> TYPE: PRT
<213> ORGANISM: Listeria monocytogenes

<400> SEQUENCE: 27

Met Leu Lys Lys Thr Ile Ala Ala Ala Leu Ala Ala Gly Leu Leu

-continued

```
                1               5                  10                 15
          Leu Ile Phe Ser Pro Phe Ile Lys Asn Gly Ile Val Lys Tyr Met Ser
                         20                  25                 30
          Gly His Glu Thr Ile Glu Gln Tyr Lys Ala Ser Asp Ile Lys Lys Asn
                         35                  40                 45
          Asn Glu Lys Asp Ala Thr Phe Asp Phe Glu Ser Val Gln Leu Pro Ser
                    50                  55                 60
          Met Thr Ser Val Ile Lys Gly Ala Ala Asn Tyr Asp Lys Asp Ala Val
           65                  70                  75                 80
          Val Gly Ser Ile Ala Val Pro Ser Val Asp Val Asn Leu Leu Val Phe
                              85                  90                 95
          Lys Gly Thr Asn Thr Ala Asn Leu Leu Ala Gly Ala Thr Thr Met Arg
                         100                 105                110
          Ser Asp Gln Val Met Gly Lys Gly Asn Tyr Pro Leu Ala Gly His His
                         115                 120                125
          Met Arg Asp Glu Ser Met Leu Phe Gly Pro Ile Met Lys Val Lys Lys
                         130                 135                140
          Gly Asp Lys Ile Tyr Leu Thr Asp Leu Glu Asn Leu Tyr Glu Tyr Thr
          145                 150                 155                160
          Val Thr Glu Thr Lys Thr Ile Asp Glu Thr Glu Val Ser Val Ile Asp
                         165                 170                175
          Asn Thr Lys Asp Ala Arg Ile Thr Leu Ile Thr Cys Asp Lys Pro Thr
                         180                 185                190
          Glu Thr Thr Lys Arg Phe Val Ala Val Gly Glu Leu Glu Lys Thr Glu
                         195                 200                205
          Lys Leu Thr Lys Glu Leu Glu Asn Lys Tyr Phe Pro Ser Lys
                         210                 215                220

<210> SEQ ID NO 28
<211> LENGTH: 2
<212> TYPE: PRT
<213> ORGANISM: Artificial Sequence
<220> FEATURE:
<223> OTHER INFORMATION: oligogylcine

<400> SEQUENCE: 28

Gly Gly
1

<210> SEQ ID NO 29
<211> LENGTH: 3
<212> TYPE: PRT
<213> ORGANISM: Artificial Sequence
<220> FEATURE:
<223> OTHER INFORMATION: oligoglycine

<400> SEQUENCE: 29

Gly Gly Gly
1

<210> SEQ ID NO 30
<211> LENGTH: 4
<212> TYPE: PRT
<213> ORGANISM: Artificial Sequence
<220> FEATURE:
<223> OTHER INFORMATION: oligoglycine

<400> SEQUENCE: 30

Gly Gly Gly Gly
1
```

```
<210> SEQ ID NO 31
<211> LENGTH: 5
<212> TYPE: PRT
<213> ORGANISM: Artificial Sequence
<220> FEATURE:
<223> OTHER INFORMATION: oligoglycine

<400> SEQUENCE: 31

Gly Gly Gly Gly Gly
1               5

<210> SEQ ID NO 32
<211> LENGTH: 12
<212> TYPE: PRT
<213> ORGANISM: Artificial Sequence
<220> FEATURE:
<223> OTHER INFORMATION: hexa-histidine tag with linker

<400> SEQUENCE: 32

Met Arg Gly Ser His His His His His His Gly Ser
1               5                   10

<210> SEQ ID NO 33
<211> LENGTH: 249
<212> TYPE: PRT
<213> ORGANISM: Streptococcus pyogenes

<400> SEQUENCE: 33

Met Val Lys Lys Gln Lys Arg Lys Ile Lys Ser Met Ser Trp Ala
1               5                   10                  15

Arg Lys Leu Leu Ile Ala Val Leu Ile Leu Gly Leu Ala Leu Leu
                20                  25                  30

Phe Asn Lys Pro Ile Arg Asn Thr Leu Ile Ala Arg Asn Ser Asn Lys
                35                  40                  45

Tyr Gln Val Thr Lys Val Ser Lys Lys Gln Ile Lys Lys Asn Lys Glu
    50                  55                  60

Ala Lys Ser Thr Phe Asp Phe Gln Ala Val Glu Pro Val Ser Thr Glu
65                  70                  75                  80

Ser Val Leu Gln Ala Gln Met Ala Ala Gln Leu Pro Val Ile Gly
                85                  90                  95

Gly Ile Ala Ile Pro Glu Leu Gly Ile Asn Leu Pro Ile Phe Lys Gly
                100                 105                 110

Leu Gly Asn Thr Glu Leu Ile Tyr Gly Ala Gly Thr Met Lys Glu Glu
                115                 120                 125

Gln Val Met Gly Gly Glu Asn Asn Tyr Ser Leu Ala Ser His His Ile
    130                 135                 140

Phe Gly Ile Thr Gly Ser Ser Gln Met Leu Phe Ser Pro Leu Glu Arg
145                 150                 155                 160

Ala Gln Asn Gly Met Ser Ile Tyr Leu Thr Asp Lys Glu Lys Ile Tyr
                165                 170                 175

Glu Tyr Ile Ile Lys Asp Val Phe Thr Val Ala Pro Glu Arg Val Asp
                180                 185                 190

Val Ile Asp Asp Thr Ala Gly Leu Lys Glu Val Thr Leu Val Thr Cys
                195                 200                 205

Thr Asp Ile Glu Ala Thr Glu Arg Ile Ile Val Lys Gly Glu Leu Lys
    210                 215                 220

Thr Glu Tyr Asp Phe Asp Lys Ala Pro Ala Asp Val Leu Lys Ala Phe
225                 230                 235                 240
```

Asn His Ser Tyr Asn Gln Val Ser Thr
                245

<210> SEQ ID NO 34
<211> LENGTH: 178
<212> TYPE: PRT
<213> ORGANISM: Artificial Sequence
<220> FEATURE:
<223> OTHER INFORMATION: Staphylococcus aureus Sortase A shortened
      version N(2-29)

<400> SEQUENCE: 34

Met Asp Asn Tyr Leu His Asp Lys Asp Lys Asp Glu Lys Ile Glu Gln
1               5                   10                  15

Tyr Asp Lys Asn Val Lys Glu Gln Ala Ser Lys Asp Lys Lys Gln Gln
                20                  25                  30

Ala Lys Pro Gln Ile Pro Lys Asp Lys Ser Lys Val Ala Gly Tyr Ile
            35                  40                  45

Glu Ile Pro Asp Ala Asp Ile Lys Glu Pro Val Tyr Pro Gly Pro Ala
    50                  55                  60

Thr Pro Glu Gln Leu Asn Arg Gly Val Ser Phe Ala Glu Glu Asn Glu
65                  70                  75                  80

Ser Leu Asp Asp Gln Asn Ile Ser Ile Ala Gly His Thr Phe Ile Asp
                85                  90                  95

Arg Pro Asn Tyr Gln Phe Thr Asn Leu Lys Ala Ala Lys Lys Gly Ser
            100                 105                 110

Met Val Tyr Phe Lys Val Gly Asn Glu Thr Arg Lys Tyr Lys Met Thr
        115                 120                 125

Ser Ile Arg Asp Val Lys Pro Thr Asp Val Gly Val Leu Asp Glu Gln
    130                 135                 140

Lys Gly Lys Asp Lys Gln Leu Thr Leu Ile Thr Cys Asp Asp Tyr Asn
145                 150                 155                 160

Glu Lys Thr Gly Val Trp Glu Lys Arg Lys Ile Phe Val Ala Thr Glu
                165                 170                 175

Val Lys

<210> SEQ ID NO 35
<211> LENGTH: 222
<212> TYPE: PRT
<213> ORGANISM: Listeria monocytogenes

<400> SEQUENCE: 35

Met Leu Lys Lys Thr Ile Ala Ala Ala Leu Ala Ala Gly Leu Leu
1               5                   10                  15

Leu Ile Phe Ser Pro Phe Ile Lys Asn Gly Ile Val Lys Tyr Met Ser
                20                  25                  30

Gly His Glu Thr Ile Glu Gln Tyr Lys Ala Ser Asp Ile Lys Lys Asn
            35                  40                  45

Asn Glu Lys Asp Ala Thr Phe Asp Phe Glu Ser Val Gln Leu Pro Ser
        50                  55                  60

Met Thr Ser Val Ile Lys Gly Ala Ala Asn Tyr Asp Lys Asp Ala Val
65                  70                  75                  80

Val Gly Ser Ile Ala Val Pro Ser Val Asp Val Asn Leu Leu Val Phe
                85                  90                  95

Lys Gly Thr Asn Thr Ala Asn Leu Leu Ala Gly Ala Thr Thr Met Arg
            100                 105                 110

```
Ser Asp Gln Val Met Gly Lys Gly Asn Tyr Pro Leu Ala Gly His His
            115                 120                 125

Met Arg Asp Glu Ser Met Leu Phe Gly Pro Ile Met Lys Val Lys Lys
    130                 135                 140

Gly Asp Lys Ile Tyr Leu Thr Asp Leu Glu Asn Leu Tyr Glu Tyr Thr
145                 150                 155                 160

Val Thr Glu Thr Lys Thr Ile Asp Glu Thr Glu Val Ser Val Ile Asp
                165                 170                 175

Asp Thr Lys Asp Ala Arg Ile Thr Leu Ile Thr Cys Asp Lys Pro Thr
            180                 185                 190

Glu Thr Thr Lys Arg Phe Val Ala Val Gly Glu Leu Glu Lys Thr Glu
        195                 200                 205

Lys Leu Thr Lys Glu Leu Glu Asn Lys Tyr Phe Pro Ser Lys
    210                 215                 220

<210> SEQ ID NO 36
<211> LENGTH: 173
<212> TYPE: PRT
<213> ORGANISM: Artificial Sequence
<220> FEATURE:
<223> OTHER INFORMATION: Listeria monocytogenes Sortase A shortened
      variant A

<400> SEQUENCE: 36

Glu Lys Asp Ala Thr Phe Asp Phe Glu Ser Val Gln Leu Pro Ser Met
1               5                   10                  15

Thr Ser Val Ile Lys Gly Ala Ala Asn Tyr Asp Lys Asp Ala Val Val
            20                  25                  30

Gly Ser Ile Ala Val Pro Ser Val Asp Val Asn Leu Leu Val Phe Lys
        35                  40                  45

Gly Thr Asn Thr Ala Asn Leu Leu Ala Gly Ala Thr Thr Met Arg Ser
    50                  55                  60

Asp Gln Val Met Gly Lys Gly Asn Tyr Pro Leu Ala Gly His His Met
65                  70                  75                  80

Arg Asp Glu Ser Met Leu Phe Gly Pro Ile Met Lys Val Lys Lys Gly
                85                  90                  95

Asp Lys Ile Tyr Leu Thr Asp Leu Glu Asn Leu Tyr Glu Tyr Thr Val
            100                 105                 110

Thr Glu Thr Lys Thr Ile Asp Glu Thr Glu Val Ser Val Ile Asp Asp
        115                 120                 125

Thr Lys Asp Ala Arg Ile Thr Leu Ile Thr Cys Asp Lys Pro Thr Glu
    130                 135                 140

Thr Thr Lys Arg Phe Val Ala Val Gly Glu Leu Glu Lys Thr Glu Lys
145                 150                 155                 160

Leu Thr Lys Glu Leu Glu Asn Lys Tyr Phe Pro Ser Lys
                165                 170

<210> SEQ ID NO 37
<211> LENGTH: 156
<212> TYPE: PRT
<213> ORGANISM: Artificial Sequence
<220> FEATURE:
<223> OTHER INFORMATION: Listeria monocytogenes Sortase A shortened
      variant B

<400> SEQUENCE: 37

Ser Val Ile Lys Gly Ala Ala Asn Tyr Asp Lys Asp Ala Val Val Gly
1               5                   10                  15
```

```
Ser Ile Ala Val Pro Ser Val Asp Val Asn Leu Leu Val Phe Lys Gly
            20                  25                  30

Thr Asn Thr Ala Asn Leu Leu Ala Gly Ala Thr Thr Met Arg Ser Asp
        35                  40                  45

Gln Val Met Gly Lys Gly Asn Tyr Pro Leu Ala Gly His His Met Arg
 50                  55                  60

Asp Glu Ser Met Leu Phe Gly Pro Ile Met Lys Val Lys Lys Gly Asp
 65                  70                  75                  80

Lys Ile Tyr Leu Thr Asp Leu Glu Asn Leu Tyr Glu Tyr Thr Val Thr
                85                  90                  95

Glu Thr Lys Thr Ile Asp Glu Thr Glu Val Ser Val Ile Asp Asp Thr
            100                 105                 110

Lys Asp Ala Arg Ile Thr Leu Ile Thr Cys Asp Lys Pro Thr Glu Thr
        115                 120                 125

Thr Lys Arg Phe Val Ala Val Gly Glu Leu Glu Lys Thr Glu Lys Leu
130                 135                 140

Thr Lys Glu Leu Glu Asn Lys Tyr Phe Pro Ser Lys
145                 150                 155

<210> SEQ ID NO 38
<211> LENGTH: 150
<212> TYPE: PRT
<213> ORGANISM: Artificial Sequence
<220> FEATURE:
<223> OTHER INFORMATION: Listeria monocytogenes Sortase A shortened
      variant C

<400> SEQUENCE: 38

Ala Asn Tyr Asp Lys Asp Ala Val Val Gly Ser Ile Ala Val Pro Ser
1               5                   10                  15

Val Asp Val Asn Leu Leu Val Phe Lys Gly Thr Asn Thr Ala Asn Leu
            20                  25                  30

Leu Ala Gly Ala Thr Thr Met Arg Ser Asp Gln Val Met Gly Lys Gly
        35                  40                  45

Asn Tyr Pro Leu Ala Gly His His Met Arg Asp Glu Ser Met Leu Phe
 50                  55                  60

Gly Pro Ile Met Lys Val Lys Lys Gly Asp Lys Ile Tyr Leu Thr Asp
65                  70                  75                  80

Leu Glu Asn Leu Tyr Glu Tyr Thr Val Thr Glu Thr Lys Thr Ile Asp
                85                  90                  95

Glu Thr Glu Val Ser Val Ile Asp Asp Thr Lys Asp Ala Arg Ile Thr
            100                 105                 110

Leu Ile Thr Cys Asp Lys Pro Thr Glu Thr Thr Lys Arg Phe Val Ala
        115                 120                 125

Val Gly Glu Leu Glu Lys Thr Glu Lys Leu Thr Lys Glu Leu Glu Asn
    130                 135                 140

Lys Tyr Phe Pro Ser Lys
145                 150

<210> SEQ ID NO 39
<211> LENGTH: 137
<212> TYPE: PRT
<213> ORGANISM: Artificial Sequence
<220> FEATURE:
<223> OTHER INFORMATION: Listeria monocytogenes Sortase A shortened
      variant D

<400> SEQUENCE: 39
```

Ala Asn Tyr Asp Lys Asp Ala Val Val Gly Ser Ile Ala Val Pro Ser
1               5                   10                  15

Val Asp Val Asn Leu Leu Val Phe Lys Gly Thr Asn Thr Ala Asn Leu
            20                  25                  30

Leu Ala Gly Ala Thr Thr Met Arg Ser Asp Gln Val Met Gly Lys Gly
        35                  40                  45

Asn Tyr Pro Leu Ala Gly His His Met Arg Asp Glu Ser Met Leu Phe
    50                  55                  60

Gly Pro Ile Met Lys Val Lys Lys Gly Asp Lys Ile Tyr Leu Thr Asp
65                  70                  75                  80

Leu Glu Asn Leu Tyr Glu Tyr Thr Val Thr Glu Thr Lys Thr Ile Asp
                85                  90                  95

Glu Thr Glu Val Ser Val Ile Asp Asp Thr Lys Asp Ala Arg Ile Thr
            100                 105                 110

Leu Ile Thr Cys Asp Lys Pro Thr Glu Thr Thr Lys Arg Phe Val Ala
            115                 120                 125

Val Gly Glu Leu Glu Lys Thr Glu Lys
        130                 135

<210> SEQ ID NO 40
<211> LENGTH: 141
<212> TYPE: PRT
<213> ORGANISM: Artificial Sequence
<220> FEATURE:
<223> OTHER INFORMATION: Listeria monocytogenes Sortase A shortened
      variant E

<400> SEQUENCE: 40

Gly Ser Ile Ala Val Pro Ser Val Asp Val Asn Leu Leu Val Phe Lys
1               5                   10                  15

Gly Thr Asn Thr Ala Asn Leu Leu Ala Gly Ala Thr Thr Met Arg Ser
            20                  25                  30

Asp Gln Val Met Gly Lys Gly Asn Tyr Pro Leu Ala Gly His His Met
        35                  40                  45

Arg Asp Glu Ser Met Leu Phe Gly Pro Ile Met Lys Val Lys Lys Gly
50                  55                  60

Asp Lys Ile Tyr Leu Thr Asp Leu Glu Asn Leu Tyr Glu Tyr Thr Val
65                  70                  75                  80

Thr Glu Thr Lys Thr Ile Asp Glu Thr Glu Val Ser Val Ile Asp Asp
                85                  90                  95

Thr Lys Asp Ala Arg Ile Thr Leu Ile Thr Cys Asp Lys Pro Thr Glu
            100                 105                 110

Thr Thr Lys Arg Phe Val Ala Val Gly Glu Leu Glu Lys Thr Glu Lys
            115                 120                 125

Leu Thr Lys Glu Leu Glu Asn Lys Tyr Phe Pro Ser Lys
        130                 135                 140

<210> SEQ ID NO 41
<211> LENGTH: 5
<212> TYPE: PRT
<213> ORGANISM: Artificial Sequence
<220> FEATURE:
<223> OTHER INFORMATION: LPXTA sortase-motif
<220> FEATURE:
<221> NAME/KEY: MISC_FEATURE
<222> LOCATION: (3)..(3)
<223> OTHER INFORMATION: X can be any amino acid residue

<400> SEQUENCE: 41

```
Leu Pro Xaa Thr Ala
1               5

<210> SEQ ID NO 42
<211> LENGTH: 5
<212> TYPE: PRT
<213> ORGANISM: Artificial Sequence
<220> FEATURE:
<223> OTHER INFORMATION: sortase-motif

<400> SEQUENCE: 42

Leu Pro Glu Thr Ala
1               5

<210> SEQ ID NO 43
<211> LENGTH: 5
<212> TYPE: PRT
<213> ORGANISM: Artificial Sequence
<220> FEATURE:
<223> OTHER INFORMATION: sortase-motif

<400> SEQUENCE: 43

Leu Pro Lys Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: sortase-motif

<400> SEQUENCE: 44

Leu Pro Lys Thr Ala
1               5
```